United States Patent
Ramamurthy et al.

(10) Patent No.: US 6,193,659 B1
(45) Date of Patent: Feb. 27, 2001

(54) MEDICAL ULTRASONIC DIAGNOSTIC IMAGING METHOD AND APPARATUS

(75) Inventors: Bhaskar S. Ramamurthy, San Jose; Charles Bradley, Burlingame; Ken Sawatari, Mountain View; Danhua Zhao, Milpitas; Stuart L. Carp, Menlo Park; Stirling S. Dodd, San Jose; David J. Hedberg, Menlo Park; Samuel H. Maslak, Woodside; Daniel E. Need, Mountain View, all of CA (US)

(73) Assignee: Acuson Corporation, Mountain View, CA (US)

(*) Notice: Subject to any disclaimer, the term of this patent is extended or adjusted under 35 U.S.C. 154(b) by 0 days.

(21) Appl. No.: 09/282,397

(22) Filed: Mar. 31, 1999

Related U.S. Application Data

(63) Continuation-in-part of application No. 09/191,034, filed on Nov. 12, 1998, now abandoned, which is a continuation of application No. 08/893,271, filed on Jul. 15, 1997, now abandoned.
(60) Provisional application No. 60/095,768, filed on Aug. 7, 1998.

(51) Int. Cl.[7] .................................................. A61B 8/00
(52) U.S. Cl. ............................................................ 600/443
(58) Field of Search .................................... 600/437, 443, 600/447, 455–458; 367/7, 11, 138; 73/625

(56) References Cited

U.S. PATENT DOCUMENTS

| | | |
|---|---|---|
| 4,712,037 | 12/1987 | Verbeek et al. . |
| 5,040,537 | 8/1991 | Katakura . |
| 5,111,823 | 5/1992 | Cohen . |

(List continued on next page.)

FOREIGN PATENT DOCUMENTS

| | | |
|---|---|---|
| 0 357 164 | 3/1990 | (EP) . |
| 0 770 352 A1 | 5/1997 | (EP) . |

OTHER PUBLICATIONS

Pi Hsien Chang, et al., "Second Harmonic Imaging and Harmonic Doppler Measurements with Albunex." IEEE Transactions on Ultrasonics, Ferroelectrics, and Frequency Control, vol. 42, No. 6, Nov. 1995.

(List continued on next page.)

*Primary Examiner*—Marvin M. Lateef
*Assistant Examiner*—Ali M. Imam
(74) *Attorney, Agent, or Firm*—Brinks Hofer Gilson & Lione

(57) ABSTRACT

An improvement to the method for harmonic imaging including the steps of (a) transmitting ultrasonic energy at a fundamental frequency and (b) receiving reflected ultrasonic energy at a harmonic of the fundamental frequency is provided. The transmitting step includes the step of: applying the plurality of waveforms to a respective plurality of transducer elements, a first waveform of the plurality of waveforms characterized by a first value of a harmonic power ratio, waveforms transmitted from the transducer elements and corresponding to the plurality of waveforms summing as an acoustic waveform substantially at the point, the acoustic waveform characterized by a second value of the harmonic power ratio less than the first value. The imaging method can also include a step for subdividing the transmit aperture into two or more subapertures, each subaperture having at least four adjacent transducer elements. The subapertures are phased differently with respect to one another to selectively reduce either fundamental components or harmonic components of echoes from tissue. These techniques can be used to improve contrast agent harmonic imaging as well as tissue harmonic imaging, depending upon the phase shift selected.

73 Claims, 16 Drawing Sheets

U.S. PATENT DOCUMENTS

| | | |
|---|---|---|
| 5,115,809 | 5/1992 | Saitoh et al. . |
| 5,190,766 | 3/1993 | Ishihara . |
| 5,195,520 | 3/1993 | Schlief et al. . |
| 5,215,680 | 6/1993 | D'Arrigo . |
| 5,219,401 | 6/1993 | Cathignol et al. . |
| 5,255,683 | 10/1993 | Monaghan . |
| 5,358,466 | 10/1994 | Aida et al. . |
| 5,379,642 * | 1/1995 | Reckwerdt et al. ............ 73/625 |
| 5,380,411 | 1/1995 | Schlief . |
| 5,410,205 | 4/1995 | Gururaja . |
| 5,410,516 | 4/1995 | Uhlendorf et al. . |
| 5,417,214 | 5/1995 | Roberts et al. . |
| 5,425,366 | 6/1995 | Reinhardt et al. . |
| 5,433,207 | 7/1995 | Pretlow, III . |
| 5,438,554 | 8/1995 | Seyed-Bolorforosh et al. . |
| 5,456,255 | 10/1995 | Abe et al. . |
| 5,456,257 | 10/1995 | Johnson et al. . |
| 5,469,849 | 11/1995 | Sasaki et al. . |
| 5,479,926 | 1/1996 | Ustuner et al. . |
| 5,482,046 | 1/1996 | Deitrich . |
| 5,523,058 | 6/1996 | Umemura et al. . |
| 5,526,816 | 6/1996 | Arditi . |
| 5,558,092 | 9/1996 | Unger et al. . |
| 5,560,364 | 10/1996 | Porter . |
| 5,577,505 | 11/1996 | Brock-Fisher et al. . |
| 5,579,768 | 12/1996 | Klesenski . |
| 5,579,770 | 12/1996 | Finger . |
| 5,580,575 | 12/1996 | Unger et al. . |
| 5,601,086 | 2/1997 | Pretlow, III et al. . |
| 5,608,690 | 3/1997 | Hossack et al. . |
| 5,617,862 | 4/1997 | Cole et al. . |
| 5,632,277 | 5/1997 | Chapman et al. . |
| 5,640,959 * | 6/1997 | Hara et al. .................... 600/447 |
| 5,675,554 | 10/1997 | Cole et al. . |
| 5,678,554 | 10/1997 | Hossack et al. . |
| 5,696,737 | 12/1997 | Hossack et al. . |
| 5,706,819 | 1/1998 | Hwang et al. . |
| 5,724,976 | 3/1998 | Mine et al. . |
| 5,740,128 | 4/1998 | Hossack et al. . |
| 5,833,613 | 11/1998 | Averkiou et al. . |
| 5,833,614 | 11/1998 | Dodd et al. . |
| 5,913,823 | 6/1999 | Hossack et al. . |
| 6,045,506 * | 4/2000 | Hossack ...................... 600/443 |

OTHER PUBLICATIONS

Marc Gensane, "Bubble population measurements with a parametric array." J. Acoustical Society of America, 95 (6), Jun. 1994.

Ken Ishihara, et al., "New Approach to Noninvasive Manometry Based on Pressure Dependent Resonant Shift of Elastic Mirocapsules in Ultrasonic Frequency Characteristics." Japanese J. of Applied Physics, vol. 2 (1988).

V.L. Newhouse, et al., "Bubble size measurements using the nonlinear mixing of two frequencies." J. Acoustical Society of America, 75 (5), May 1984.

"Small Spheres Lead to Big Ideas." Research News, Science vol. 267, Jan. 20, 1995.

Abstracts Journal of the American Society of Echocardiography, vol. 8, No. 3 pp. 345–346, 355, 358–364.

Deborah J. Rubens, MD, et al., "Sonoelasticity Imaging of Prostate Cancer: In Vitro Results." Radiology, vol. 195, No. 2, 1995.

B. Schrope, et al., "Simulated Capillary Blood Flow Measurement Using a Nonlinear Ultrasonic Contrast Agent." Ultrasonic Imaging 14 (1992).

Fred Lee, Jr., MD, et al., "Sonoelasticity Imaging: Results in in Vitro Tissue Specimens." Radiology, vol. 181, No. 1 (1991).

Kevin J. Parker, PhD., et al., "Sonoelasticity of Organs: Shear Waves Ring A Bell." J. Ultrasound Med., 11 (1992).

William Armstrong, M.D., et al., "Position Paper on Contrast Echocardiography." American Society of Echocardiography, draft 1, Jun. 6, 1994.

K.J. Parker, et al., "Tissue Response to Mechanical Vibrations for 'Sonoelasticity Imaging'." Ultrasound in Med. and Biol., vol. 16, No. 3, (1990).

Robert M. Lerner, et al., "'Sonoelasticity' Images Derived from Ultrasound Signals in Mechanically Vibrated Tissus." Ultrasound in Med. and Biol., vol. 16, No. 3 (1990).

Excerpt from Ultrasonics: Fundamentals and Applications (1992), pp. 380–393, 363–365.

J.A. Hossack et al., "Improving Transducer Performance Using Multiple Active Layers." SPIE vol. 1733 (1992).

Volkmar Uhlendorf, et al., "Nonlinear Acoustical Response of Coated Microbubbles in Diagnostic Ultrasound." IEEE 1994 Ultrasonics Symposium.

John A. Hossack, et al., "Improving the Characteristics of a Transducer Using Multiple Piezoelectric Layers." IEEE Transactions on Ultrasonics, Ferroelectrics, and Frequency Control, vol. 40, No. 2, Mar. 1993.

H. Edward Karrer, et al., "A Phased Array Acoustic Imaging System for Medical Use." IEEE 1980 Ultrasonics Symposium.

"HP Ultrasound Technologies—Viability." About HP Ultrasound Imaging, WWW document, 1997.

Ted Christopher, "Finite Amplitude Distortion–Based Inhomogeneous Pulse Echo Ultrasonic Imaging." IEEE Transactions on Ultrasonics, Ferroelectrics, and Frequency Control. vol. 44, No. 1, Jan. 1997.

"Supplement to Journal of the American College of Cardiology." American College of Cardiology, 45th Annual Scientific Session, Mar. 24–27, 1996 pp. 1996 pp. 21A, 63A, 239–240A.

Yang–Sub Lee, et al., "Time–Domain Modeling of Pulsed Finite–Amplitude Sound Beams." J. Acoustical Society of America, 97 (2), Feb. 1995.

Michalakis A. Averkiou, et al., "Self–Demodulation of Amplitude and Frequency–Modulated Pulses in a Thermoviscous Fluid." J. Acoustical Society of America, 94 (5), Nov. 1993.

S. Krishnan and M. O'Donnell, "Transmit Aperture Processing for Nonlinear Contrast Agent Imaging", 1996, pp. 77–105.

* cited by examiner

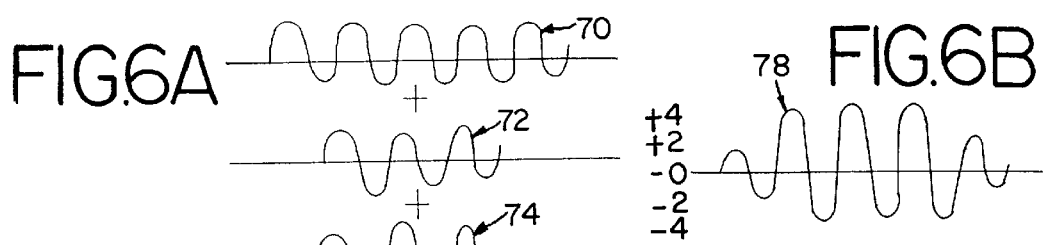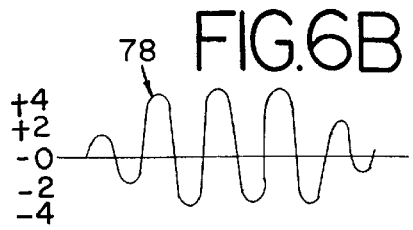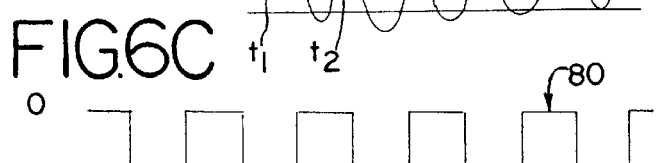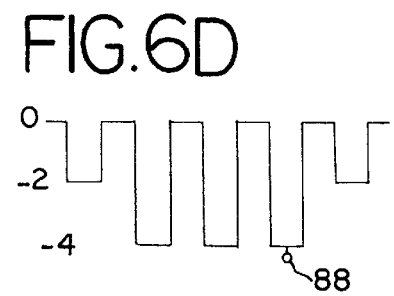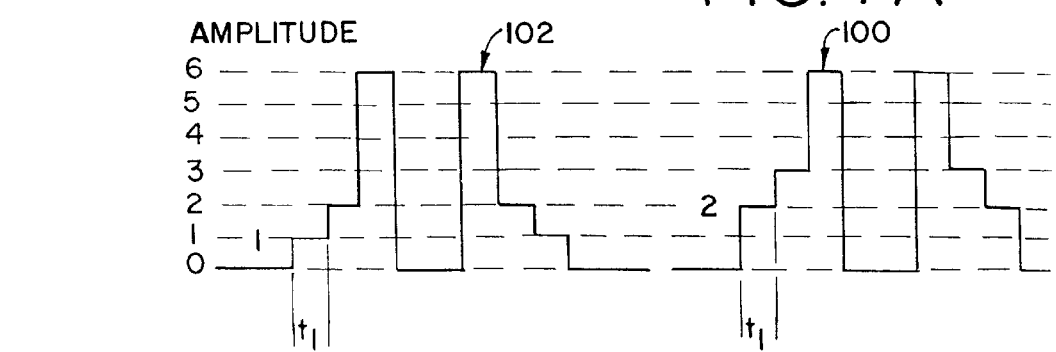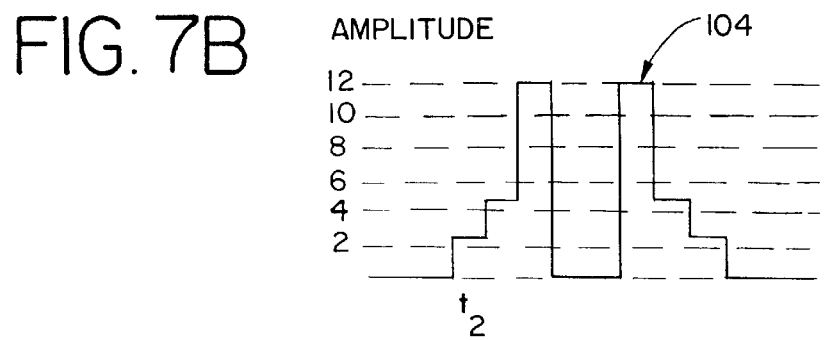

PULSE STRUCTURE AT t=0.0/1.54mm/µs

PULSE STRUCTURE AT t=5.0 mm/1.54mm/µs

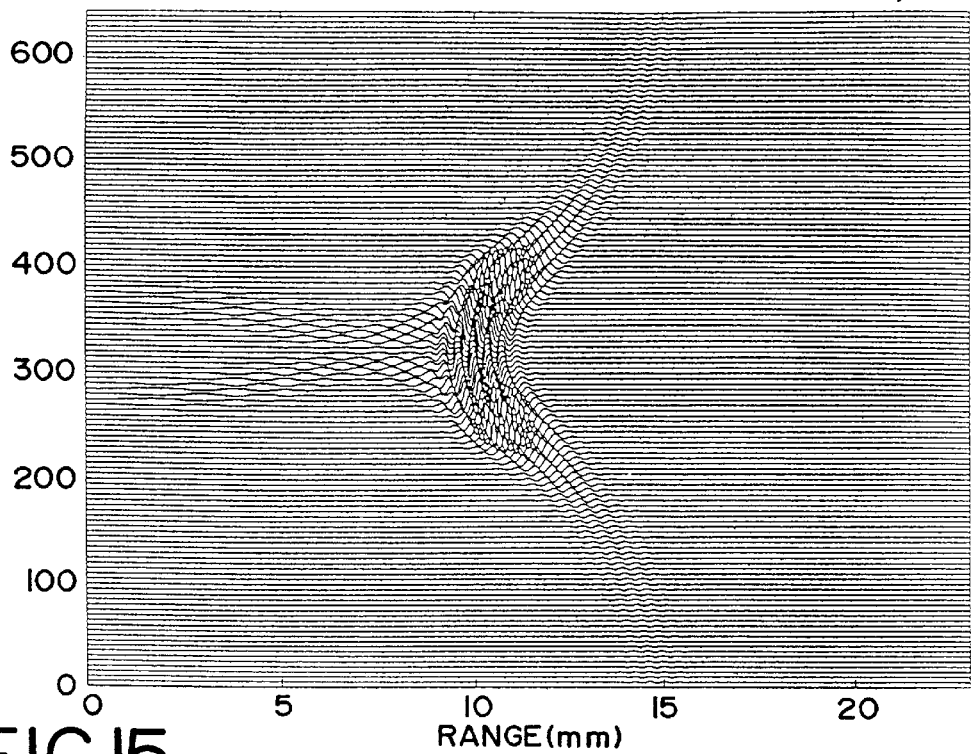
FIG.14 (PRIOR ART) PULSE STRUCTURE AT t=10.0mm/1.54mm/μs
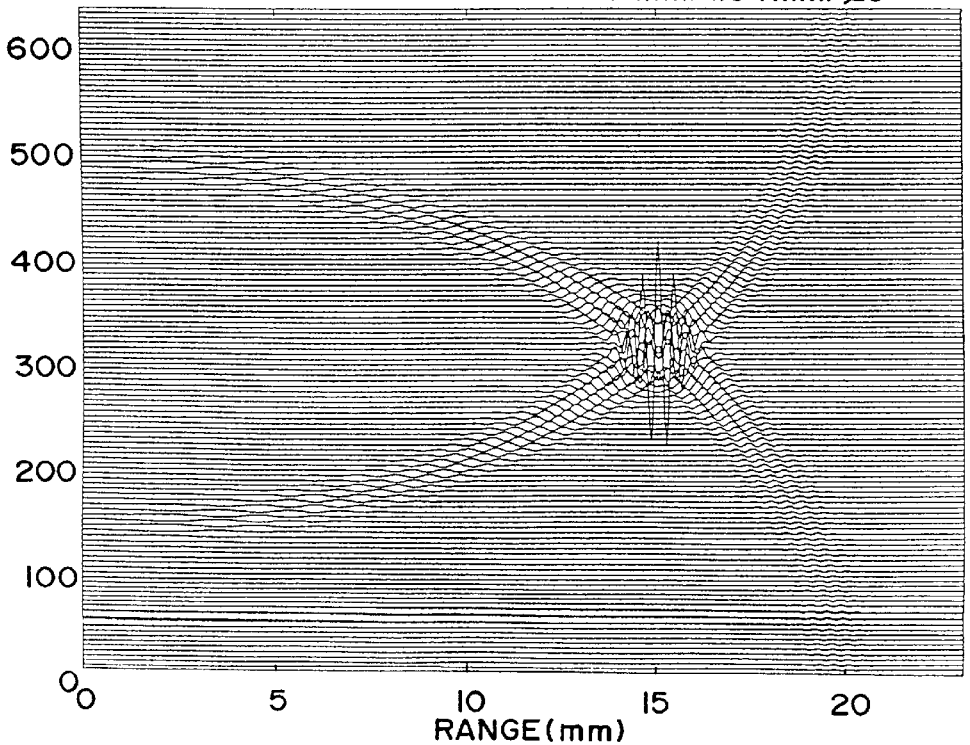
FIG.15 (PRIOR ART) PULSE STRUCTURE AT t=15.0mm/1.54mm/μs

MEDICAL ULTRASONIC DIAGNOSTIC IMAGING METHOD AND APPARATUS

This application is a continuation-in-part of U.S. application Ser. No. 09/191,034, now abandoned, filed Nov. 12, 1998, which is a continuation of U.S. application Ser. No. 08/893,271, filed Jul. 15, 1997 now abandoned; and this application claims the benefit of the filing date pursuant to 35 U.S.C. §119(e) of Provisional Application Ser. No. 60/095,768, filed Aug. 7, 1998, the disclosure of which is hereby incorporated by reference.

BACKGROUND

I. This invention generally relates to ultrasound imaging systems. In particular, the invention relates to improved systems and methods for imaging using harmonic frequency signals.

Ultrasound imaging systems generate and transmit ultrasound signals. The systems typically have several imaging modes, such as B-mode, color flow, and spectral Doppler.

The transmitted ultrasound signals have optimal characteristics set in response to the selected mode. The characteristics include frequency and bandwidth. As an example, B-mode imaging uses transmitted signals with a wide bandwidth and high frequency. As another example, color flow imaging uses transmitted signals with narrow bandwidth and lower frequency as compared to B-mode imaging.

Another type of imaging is harmonic imaging. Harmonic imaging is generally associated with imaging tissue or contrast agents at harmonic frequencies.

Typically, the transmitted ultrasound signal is a burst of sinusoidal waves associated with rectangular or sinusoidal transmit waveforms applied to the transducer. The transmitted signal has a center frequency within the 1 to 15 MHz range. The ultrasound signal propagates through a body. The ultrasound signal reflects off structures within the body, such as tissue boundaries. Some of the reflected signals, or echo signals, propagate back towards the transducer.

As the transmit signal propagates through and scatters within the body, additional frequency components are generated, such as at harmonics of the transmit frequency. These additional frequency components continue to propagate through and reflect off structures in the body. Echo signals having the same frequencies as the transmit signal and echo signals associated with the additional frequency components impinge on the transducer. The additional frequency components are caused by non-linear effects, such as non-linear propagation.

The harmonic signals may also be generated by ultrasound contrast agents. The contrast agents are typically gas or fluid filled micro-spheres which resonate at ultrasound frequencies. The contrast agents are injected in the blood stream and carried to various locations in the body. When insonified, harmonic echo signals are generated due to resonance within the contrast agents.

The echo signals are received, processed and detected by the ultrasound system. For harmonic imaging, energies associated with fundamental or transmit frequencies are removed by receive filtering. Thus, echo signals resulting from non-linear propagation and reflection are detected by the ultrasound system. However, the transmitted burst may include significant energy at the harmonic frequencies. The transmitted energy masks the non-linear response of the body and interferes with the harmonic signals from any contrast agents.

To improve harmonic imaging, it is known to reduce the energy at the harmonic in the transmit burst. The energy at the harmonic is reduced by generating a Gaussian envelope, complex sinusoidal waveform for each channel of a transducer. However, transmit beamformers capable of generating such a complex waveform require expensive components.

The present invention is directed to further improvements that enhance the imaging of the non-linear response of a body.

II. The present invention relates to medical diagnostic ultrasonic imaging systems, and in particular to transmit techniques that selectively suppress fundamental or harmonic energy in the backscattered signal.

Previous methods used to reject the fundamental signal component in tissue harmonic imaging are classical filtering and two-pulse methods. In the two-pulse method (Chapman U.S. Pat. No. 5,632,277, Hwang U.S. Pat. No. 5,706,819), two pulses are transmitted in sequence, the second being substantially identical to the first but inverted. The received signals are then added at some point in the receive signal path prior to amplitude detection. The result is a reduction in the level of the fundamental component of the signal and an increase in the second harmonic component.

Previous methods used to reject the tissue harmonic signal component in contrast agent imaging include waveform pre-distortion. In waveform predistortion, a second harmonic component is included in the signal that is launched from the transducer in order to cancel the tissue harmonic signal. Such an approach requires the functional form of the transmit signal to be dependent upon the transmit power level, the transmit aperture, and other parameters. In addition, the waveform pre-distortion method only suppresses the tissue harmonic signal over a limited range.

SUMMARY

I. The present invention is defined by the following claims. The preferred embodiments relate to improvements to a method for harmonic imaging, where the method comprises the steps of (a) transmitting ultrasonic energy at a fundamental frequency and (b) receiving reflected ultrasonic energy at a harmonic of the fundamental frequency.

According to a first aspect of these embodiments, the transmitting step includes the step of applying the plurality of waveforms to a respective plurality of transducer elements, a first waveform of the plurality of waveforms characterized by a first value of a harmonic power ratio, waveforms transmitted from the transducer elements and corresponding to the plurality of waveforms summing as an acoustic waveform substantially at the point, the acoustic waveform characterized by a second value of the harmonic power ratio less than the first value.

According to a second aspect of these embodiments, a method of generating waveforms in the acoustic domain for harmonic imaging is provided. The method includes the steps of: transmitting at a first start time at least a first waveform comprising a first number of cycles; transmitting at a second start time at least a second waveform comprising the first number of cycles, wherein the second start time corresponds to at least a one cycle delay from the first start time; generating at a point a third waveform responsive to the first and second waveforms, the third waveform comprising a shape rising gradually to a respective value and falling gradually from the respective value.

According to a third aspect of these embodiments, a method of generating waveforms in the acoustic domain for harmonic imaging is provided. The method includes the steps of transmitting at a first start time at least a first waveform comprising a first number of cycles; transmitting at a second start time at least a second waveform comprising a second number of cycles, wherein the second number of cycles comprises at least two cycles less than the first number and the second start time corresponds to at least a one cycle delay from the first start time; generating at a point a third waveform responsive to the first and second waveforms, the third waveform comprising a shape rising gradually to a respective maximum value and falling gradually from the respective maximum value.

According to a fourth aspect of these embodiments, a method of generating waveforms in the acoustic domain for harmonic imaging is provided. The method includes the steps of: transmitting at least a first waveform comprising a first amplitude; transmitting at least a second waveform comprising a second amplitude selected relative to the first amplitude in addition to apodization; generating at a point an acoustic waveform responsive to the first and second waveforms, the third waveform comprising a shape rising gradually to a respective maximum value and falling gradually from the respective maximum value and a number of amplitude levels more than a number of amplitude levels associated with each of the first and second waveforms.

According to a fifth aspect of these embodiments, various parameters of the waveforms relative to other waveforms are varied to alter the spectral response in the acoustic domain of the summed beam. The position, bandwidth and roll-off of a null or reduction in energy at harmonic frequencies may be altered.

According to a sixth aspect of these embodiments, an improved method for (a) transmitting a plurality of waveforms from a transducer at a fundamental frequency into a target for each of a plurality of scan lines and (b) receiving reflected ultrasonic energy at a harmonic of the fundamental frequency response to step (a) is provided. Step (a) comprises changing an aperture for transmitting waveforms with different delays in addition to focusing delays as a function of an angle of one of said plurality of scan lines.

II. The present invention is defined by the following claims. The preferred embodiments described below launch first and second ultrasonic pulses towards a region. The phase difference between the first and second fundamental components of the first and second pulses, respectively, is selected to cause the first and second fundamental components to destructively interfere to a different extent than a harmonic of the fundamental components. By properly selecting the phase difference, destructive interference can be obtained between either the fundamental components or a selected harmonic of the fundamental components.

BRIEF DESCRIPTION OF THE DRAWINGS

FIG. 6A is a graphical representation of a plurality of transmit waveforms.

FIG. 6B is a graphical representation of a waveform in the acoustic domain.

FIG. 6C is a graphical representation of a plurality of transmit waveforms.

FIG. 6D is a graphical representation of a waveform in the acoustic domain.

FIG. 7A is a graphical representation of a plurality of transmit waveforms.

FIG. 7B is a graphical representation of a waveform in the acoustic domain.

FIGS. 12 through 16 are diagrams illustrating a beam structure of a fundamental pulse for a conventional aperture at successive times.

Figure 1:
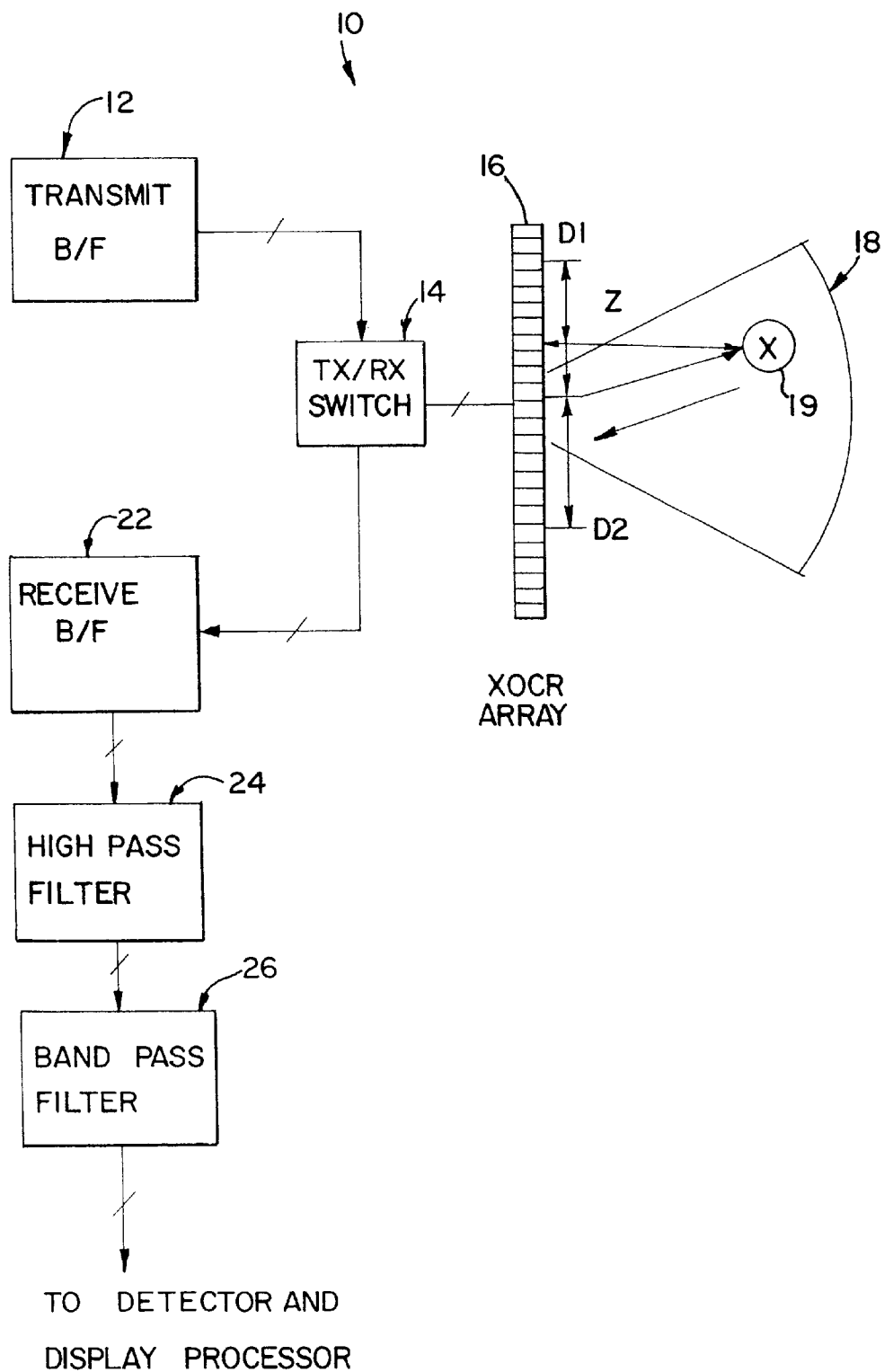
FIG. 1 is a block diagram of an ultrasound system for harmonic imaging.

DETAILED DESCRIPTION OF THE
PREFERRED EMBODIMENTS

I. The preferred embodiments described below are designed to reduce harmonic energy in the transmitted beam. Referring now to the figures, and in particular, FIG. 1, an ultrasound system is generally shown at 10. The ultrasound system 10 is configurable to transmit signals that sum in the acoustic domain with reduced energy at harmonic imaging frequencies. Harmonic frequencies are frequencies associated with non-linear propagation or scattering of the transmit signals, usually at integral harmonics such as second, third, and fourth harmonics. As used herein, harmonic includes second, third, fourth, and other harmonics of the fundamental. Non-linear propagation or scattering results in shifting energy associated with a frequency or frequencies to another frequency or frequencies. As used herein, harmonic shifting may also include energy shifted to subharmonics and fractional harmonics (e.g. ½ or ¾ of the fundamental).

The system 10 includes a transmit beamformer 12 that supplies high voltage transmit waveforms in a plurality of channels via a TX/RX switch 14 to a transducer array 16. The transmit waveforms are controlled by input information corresponding to delays, numbers of cycles, amplitude level and duty cycle. Preferably, the transmit beamformer 12 and the transducer array 16 have a broadband response and are capable of transmitting the maximum allowable acoustic power densities for better signal to noise sensitivity. The transducer array 16, which can be any suitable type, generates an ultrasonic transmit beam in the acoustic domain in response to the transmit waveforms. The transmit beam propagates outwardly through the subject 18 being imaged. The transducer 16 frequency response acts as a bandpass filter. Thus, the energies associated with harmonics higher than the harmonic of interest may be removed as the transmit waveform is radiated by the transducer 16.

Ultrasonic energy echoed by the subject 18, such as from a point 19, at the harmonic frequency is received by the transducer array 16 and focused by the receive beamformer 22. Preferably, the transducer 16 and receive beamformer 22 have a broadband response. The focused signal is preferably filtered with a high pass filter 24. The high pass filter attenuates energy associated with fundamental frequencies, which are typically greater than energies associated with harmonic frequencies. Preferably, a bandpass filter 26 further reduces energies associated with frequencies other than the desired harmonic frequencies. Other receive beamformers, both digital and analog, with different or the same filtering structures may be used. The filtered information is detected and displayed as an image by a display processor (not shown).

The harmonic image represents structure within the subject 18. The harmonic signal may be generated by tissue harmonic response or by non-linear contrast agents which may be provided within the subject 18. Tissue harmonic imaging is associated with harmonic energy generation through non-linear propagation of the transmit beam. Contrast agent harmonic imaging is associated with harmonic energy generation through interaction of the fundamental energy with the contrast agent.

All of the harmonic imaging techniques described herein can be used in both tissue and contrast agent harmonic imaging modes. In the tissue harmonic imaging mode, no additional non-linear contrast agent is added to the target, and only the non-linear characteristics of the tissue are relied on to create the ultrasonic image. Medical ultrasound imaging is typically conducted in a discrete imaging session for a given subject at a given time. For example, an imaging session can be limited to an ultrasound patient examination of a given tissue of interest over a period of ¼ to 1 hour, though other durations are possible. In this case no additional non-linear contrast agent is introduced into the tissue at any time during the imaging session.

In the contrast agent harmonic imaging mode, any one of a number of well known non-linear contrast agents such as FS069 from Molecular Biosystems, San Diego, California, can be added to the target in order to enhance the non-linear harmonic response of blood or fluid.

Figure 2:
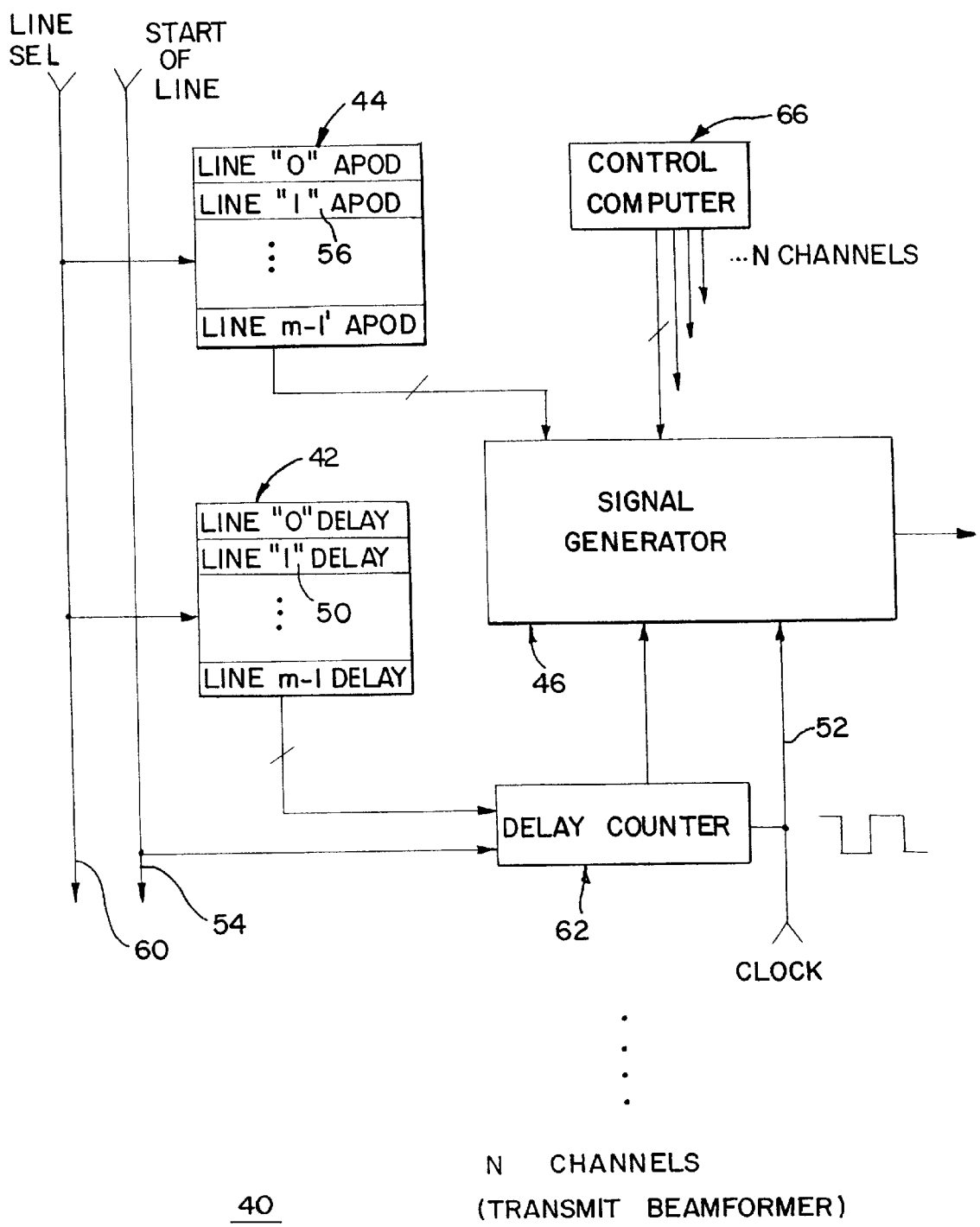
FIG. 2 is a block diagram of a transmit beamformer.

FIG. 2 shows a block diagram of a preferred embodiment 40 of the transmit beamformer 12 of FIG. 1. As shown in FIG. 2, the transmit beamformer 40 includes N channels, one for each of the transducers of the transducer array 16 (see FIG. 1). Each channel includes a delay memory 42, an apodization memory 44, a delay counter 62, and a signal generator 46. Any of the various structures may be used for a plurality of channels instead of in a single channel as in the preferred embodiment. Other embodiments may be used.

The delay memory 42 includes m delay words 50, one for each possible steering angle or ultrasound transmit scan line. Each delay word 50 of the delay memory 42 corresponds to the time delay for the transmit scan line selected and for the transducer array element connected to the appropriate transmit channel. For example, in the preferred embodiment, the delay word 50 specifies the number of transmit carrier cycles to delay after a start of line signal on line 54 before generation and transmission of the transmit waveform. As discussed below, the delay includes delay associated with focusing and delay associated with generating the desired waveform in the acoustic domain.

The delay memory 42 of FIG. 2 is not required, but reduces memory or control requirements for the signal generator 46. The delay memory 42 eliminates the need to calculate the delay or derive the delay from other parameters as the ultrasound scan line changes angles.

The apodization memory 44 includes m apodization words 56, one for each possible steering angle or ultrasound transmit scan line. Each apodization word 56 of the apodization memory 44 corresponds to an amplitude level or scaling for the particular channel and transmit scan line. Each word 56 is based on apodization formats known in the art.

A computer 66 provides set-up data associated with a selected imaging mode to the signal generator to specify the characteristics (e.g. amplitude levels and number of cycles) of the transmit waveform for the imaging mode. Other embodiments of imaging mode selection are possible. Furthermore, some systems may not provide imaging mode selection.

The signal generator 46 is of a construction known in the art for generating transmit waveforms. For example, the signal generator 46 includes control, timing, waveform generation, scaling, digital to analog conversion, and output driver circuits. Other embodiments are possible, such as the transmit beamformer disclosed in Method and Apparatus for Transmit Beamformer System, U.S. patent application Ser. No. 08/673,410, filed Jul. 15, 1996 or a DC switch structure. Alternative means for waveform generation also include RAM or ROM memory and logic based devices. The complexity and details of the preferred embodiment of the signal generator 46 depend on the number of timing states, apodization levels, and pulse amplitude quantization levels needed to adequately generate the desired transmit waveform. Preferably, a simple signal generator is used, such as a signal generator capable of producing two amplitude level uni-polar or three amplitude level bipolar waveforms sampled two or more times in each carrier cycle.

Referring to FIG. 2, the apodization memory 44 is not required, but allows more precise focusing and amplitude control. Without the apodization capability and associated memory 44, the functions of the signal generator 46 are simplified. In this case, the signal generator 46 outputs amplitude levels corresponding to a constant apodization weighting.

In use, control data specifying the channel timing delay words 50, apodization words 56 and any other required set-up data is provided to the transmit beamformer 40. Other set-up data is preferably provided by the computer 66, including parameters, such as a carrier frequency, a bandwidth, and other information as a function of possible timing states and apodization levels. In alternative constructions, any of the control data may be provided by alternative structures.

Based on the control data, each channel responds to a scan line selection signal on line 60 by loading the words 50 and 56 for the selected scan line. The word 50 from the delay memory 42 is loaded into the delay counter 62. Since the delay word 50 is preferably specified in fractions of a carrier cycle, the delay word 50 is used to select a finely quantized timing state corresponding to the clock phase. The delay counter 62 responds to a start of scan line signal on the line 54 by incrementing or decrementing the stored value with each cycle of the clock on the line 52. When the counter 62 counts to zero, the next cycle initiates a start signal for waveform generation. The counter 62 generates the appropriate timing states for generating a transmit waveform by the signal generator 46. The transmit waveform is characterized relative to transmit waveforms in one or more other channels.

The amount of delay (duration) prior to initiating the start signal includes information associated with focusing and reduction of energy transmitted at harmonic frequencies in the acoustic domain. For focusing, the amount of delay for one element relative to another element is a function of the distance, Z, of the focal point from the center of the transducer array 16 (see FIG. 1), the distance, D1 and D2 of each element of the transducer 16 (see FIG. 1) from the center of the transducer array 16, and the speed, C, of sound in the subject 18 (see FIG. 1). In particular, the focusing delay, $\Delta t_{12}$=(the square root of $(Z^2+D_1^2)$–the square root of $(Z^2+D_2^2)$)/C. The additional delay, or shape delay, based on reduction of energy transmitted at harmonic frequencies in the acoustic domain is discussed below.

Referring to FIG. 2, the signal generator 46 also receives the apodization word 56 from the apodization memory 44. The apodization word 56 is preferably used by the signal generator 46 as a scale factor for the generated waveform. Thus, the apodization word is used to scale the waveform amplitude levels.

Based on the set-up data, apodization, and sequencer state information, the signal generator 46 produces a waveform for transmission. The preferred signal generator 46 outputs a clocked sequence of amplitude levels, preferably two (on/off), during the active portion of the transmit pulse or pulses generation. The clocked sequence is preferably coarsely sampled, such as 2 samples per cycle. The counter 62 provides timing states for generating successive amplitude levels, duty cycle, and number of cycles in the pulse train or transmit waveform. Based on the timing states and set-up data, a waveform associated with a number of pulses and amplitude levels for each pulse is generated after the start signal is initiated. Other sampling rates may be used as discussed below. For digital signal generators, the amplitude levels of each pulse output from the signal generator 46 are represented by multiple bit words using binary code, thermometer code, gray-code, specially weighted code or a combination of the codes, as known in the art. The preferred amplitude levels are a function of apodization.

The waveform amplitude output levels are either analog or converted to analog and amplified in the signal generator 46. Preferably, the output power of the signal generator is regulated by changing the voltage or current amplification for every channel the same factor. The output of the signal generator is the transmit waveform discussed above and is applied to the respective transducer via the multiplexer (see FIG. 1). Thus, a uni-polar or bi-polar high voltage transmit waveform is generated. When the pulse train for the desired transmit waveform is complete, the counter returns to an idle state until the next start signal is received.

In an alternative method, the transmit waveform is generated without applying apodization scaling within the signal generator 46. The apodization scaling is multiplied with the output from the signal generator 46. The multiplication is performed using a multiplying digital to analog converter or other structures.

The computer 66, either in real-time or as part of the set-up, provides information for generating any of various waveforms for use with signal generators 46 of various complexity. The waveforms are shaped to suppress ultrasonic energy in a wide pass band centered at the harmonic frequency of the fundamental center frequency in the ultrasonic waveform created in the acoustic domain in response to two or more transmit waveforms.

The waveforms are preferably shaped to provide optimum fundamental band efficiency. The efficiency of a waveform is a relative measure of the spectral energy in a weighted band around the fundamental center frequency when the peak is normalized to a given value. Referring to FIG. 2, for the optimum sensitivity in tissue harmonic imaging, the transmit beamformer 40 transmits at or near the maximum allowed acoustic power density. For harmonic imaging of contrast agents, the power levels may be reduced to avoid destruction of the contrast agent. Thus, efficiency is one factor considered in designing and generating the waveform.

The complexity of the waveform is another such factor. Waveforms requiring only coarse sampling, fewer amplitude levels and less amplitude quantization accuracy for any digital to analog conversion processing require less complex and costly hardware to generate. Since a plurality of signal generators 46 are typically used, the cost difference between signal generators 46 is an important consideration.

Figure 4A:
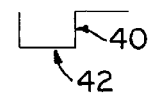
FIG. 4A is a graphical representation of a waveform.
Figure 4B:
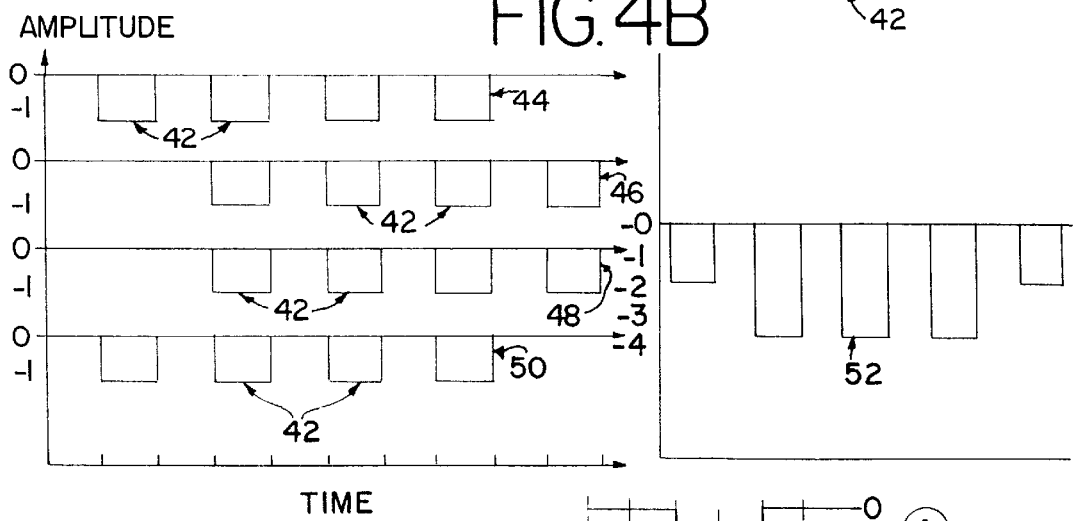
FIG. 4B is a graphical representation of a plurality of transmit waveforms and a waveform in the acoustic domain.

The transmit waveforms are either uni-polar or bi-polar. Referring to FIG. 4A, a uni-polar waveform 40 comprising one pulse 42 is shown. The transmit waveform preferably includes a plurality of pulses 42, such as the transmit waveforms 44, 46, 48 and 50 as shown in FIG. 4B. The pulses 86 and 96 correspond to intervals along the time axis where the amplitude starts at zero or anther value and then returns to zero or another value. Each pulse 86 and 96 is preferably stepped or rectangular. Stepped and rectangular pulses may include curved or other shapes. Sinusoidal waveforms or pulses of other shapes may be used, but stepped or rectangular waveforms typically require less complex transmit beamformers 12 (see FIG. 1).

The transmit waveforms are either rectangular, such as the transmit waveform 40 in FIG. 4A, or sinusoidal. Stepped rectangular waveforms, such as waveforms with multiple positive or negative amplitude levels require less complexity, but sinusoidal waveforms may be used. A rectangular waveform, such as a rectangular wave shown as the transmit waveform 40 in FIG. 4A, includes waveforms with only two amplitude levels (on/off), or uniform amplitudes, for uni-polar or three amplitude levels (positive/off/negative), or uniform amplitudes, for bi-polar. Any of the various transmit waveforms discussed above or other transmit waveforms may be used as part of the present invention.

Characteristics of the transmit waveform generated for each channel are set to enhance insonification for harmonic imaging. One or more transmit waveforms corresponding to one or more channels are generated relative to one or more other transmit waveforms corresponding to one or more other channels. The transmit waveforms are set to sum together in the acoustic domain. The summed acoustic waveform is shaped to suppress ultrasonic energy in a wide pass band centered at the harmonic frequency of the center frequency of the transmit waveform. Preferably, the summed acoustic waveform has an envelope or amplitude that gradually increases to a maximum value and gradually decreases to zero from the maximum value. The gradually increasing and decreasing envelope or amplitude corresponds to a curve or at least one step between two amplitude values, such as zero and full power. This shape reduces the energy in the spectral side lobes at the second harmonic frequencies. Other shapes of the summed acoustic waveform for reduction of transmission energies in the same or different harmonic frequencies are possible.

A calculation demonstrating the transmit waveform corruption of energies in the harmonic frequency band is a harmonic power ratio. The harmonic power ratio is the ratio of residual power of the waveform spectrum in the desired harmonic band, such as a band centered around the second order harmonic, to the power of the waveform spectrum in the corresponding fundamental band. A filter suitable for imaging is applied to the fundamental band of energies. The power of the filtered signal is calculated. The same filter is shifted and applied to the harmonic band of energies. The power of this filtered signal is also calculated. The harmonic power ratio is the ratio of these two powers. The transmit waveforms are associated with any of various harmonic power ratios. The summed acoustic waveform has a lesser harmonic power ratio than at least one of the transmit waveforms. Lower harmonic power ratios are associated with less interference from transmitted energy for harmonic imaging. Thus, by setting a characteristic of one transmit waveform relative to another, the harmonic power ratio in the acoustic domain is increased relative to the transmit waveform at one or more (or overall) transducers.

Figure 3:
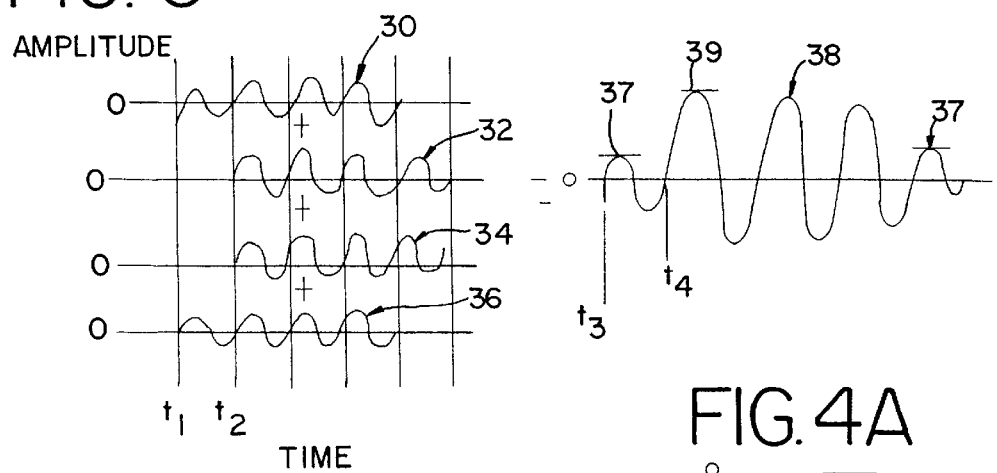
FIG. 3 is a graphical representation of a plurality of transmit waveforms and a waveform in the acoustic domain.

The characteristics of the transmit waveforms that are set relative to other transmit waveforms include the amount of delay, the number of cycles, and the amplitude. For example and referring to FIG. 3, four transmit waveforms, 30, 32, 34 and 36 having four cycles are transmitted from four transducer elements focused at a point 19 in the subject (see FIG. 1). At time t1, the first and fourth transmit waveforms 30 and 36 are transmitted. One or more complete (e.g. 1, 2, 3 . . . ) or fractional cycles (e.g. ¼, ½, ⅔, ¾ . . . ) later, such as a one cycle delay to time t2, the second and third transmit waveforms 32 and 34 are transmitted. At the point 19 within the subject 18 (see FIG. 1), the four transmit waveforms 30, 32, 34, and 36 sum represented by an acoustic waveform 38. The acoustic waveform 38 has a number of cycles corresponding to the delay plus the number of cycles of one of the transmitted waveforms, such as 5 cycles. The summation occurs naturally as known in the art.

The amplitude of the summed acoustic waveform 38 corresponds to the amplitude of the transmitted waveforms 30, 32, 34 and 36 as a function of the delay. For example, at time t3, the first and fourth waveforms 30 and 36 combine at the point. During the first cycle (t1–t2), the second and third waveforms 32 and 34 have a zero amplitude. Thus, during the first cycle in the acoustic domain (t3–t4), the amplitude 37 of the acoustic waveform 38 corresponds to the sum of the amplitudes of the first and fourth transmit waveforms 30 and 36, minus any attenuation. During the subsequent three cycles, the amplitude 39 of the acoustic waveform 38 corresponds to the summation of the amplitudes of the four transmit waveforms, 30, 32, 34, and 36, minus any attenuation. For the final, such as the fifth cycle, of the acoustic waveform 38, the first and fourth transmit waveforms 30 and 36 do not contribute to the amplitude of the acoustic waveform 38, but the second and third transmit waveforms sum. Thus, the envelope of acoustic waveform 38 starts at zero amplitude, increasing to the amplitude 37 and further to the maximum amplitude 39, then decreasing to the amplitude 37 and then further to zero amplitude.

The principle discussed above for summing transmit waveforms in the acoustic domain for harmonic imaging applies to many different transmit waveforms and more or fewer transmit waveforms. The amount of delay between waveforms may be more or less than one cycle. A plurality of delays for a plurality or more of transmit waveforms may be used. The number of cycles associated with one or more of the transmit waveforms may be different. Other amplitude shapes, or envelope shapes, of the acoustic waveform may be created, such as increasing gradually, but decreasing abruptly (e.g. by changing the second and third transmit waveforms 32 and 34 to three cycle waveforms). Furthermore, the number of steps or the rate of change of the amplitude of the acoustic waveform may be increased or decreased, respectively.

Referring to FIG. 4, the advantages of the instant invention are provided by changing the delay characteristic of one or more uni-polar waveforms relative to one or more other uni-polar waveforms. Referring to FIG. 4A, a negative rectangular pulse 42 is shown. As shown in FIG. 4B, four transmit waveforms 44, 46, 48 and 50 comprising four of the pulses 42 each are applied to the transducer. Based on a one cycle delay in transmitting the second and third waveforms 46 and 48, the amplitude or envelope of the acoustic waveform gradually increases from zero to a maximum negative value and then decreases from the maximum negative value to zero. By application of the four transmit waveforms 44, 46, 48 and 50, the acoustic waveform is generated as if the waveform 52 is applied to the transducer. Thus, a transmit beamformer 40 (see FIG. 2) with a simple DC switch signal generator 46 may produce an acoustic waveform for harmonic imaging.

Figure 5:
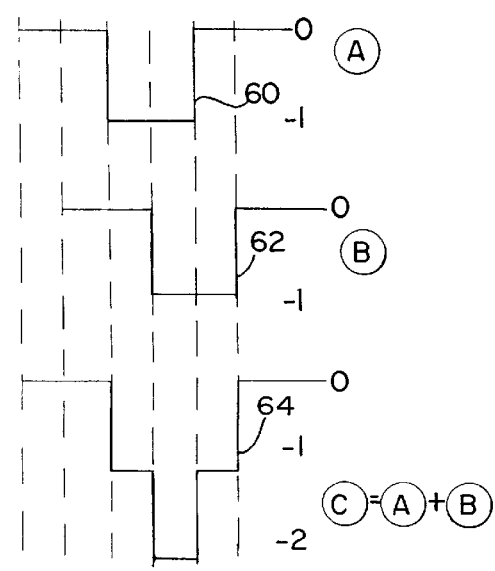
FIG. 5 is a graphical representation of a plurality of transmit waveforms and a waveform in the acoustic domain.

As another example of producing an acoustic waveform for harmonic imaging by changing the delay characteristic of one transmit waveform relative to another transmit waveform, FIG. 5 shows two transmit wave forms 60 and 62 applied to two adjacent transducer elements. Each transmit waveform comprises one negative amplitude pulse. Transmission of the second transmit waveform 62 is delayed, in addition to any focusing delay, by a ¼ cycle relative to the first transmit waveform 60. In the acoustic domain at the focal point, the first and second transmit waveforms 60 and 62 create an acoustic waveform. By application of the transmit waveforms 60 and 62, the acoustic waveform is generated as if the waveform 64 is applied to the transducer. The amplitude or envelope of the acoustic waveform increases gradually from zero to a maximum negative value and decreases from the maximum negative value to zero. Thus, the acoustic waveform results in reduced energy at the focal point due to linear propagation or scattering. While only one cycle is shown in FIG. 5, more than one cycle of the transmit waveforms 60 and 62 may be used and the corresponding more than one cycle acoustic waveform is generated. Delay of one or more transmit waveforms by a fractional cycle may be combined with the delay of one or more transmit waveforms by one or more complete cycles.

Another characteristic of the transmit waveforms that is set to provide a desired acoustic waveform is the number of cycles. For example and referring to FIGS. 6A and 6B, four acoustic waveforms 70, 72, 74, and 76 corresponding to the transmit waveforms shown in FIG. 6C are shown. The first and fourth acoustic waveforms 70 and 76 are 5 cycle waveforms. The second and third acoustic waveforms are 3 cycle waveforms. The first and fourth acoustic waveforms 70 and 76 are transmitted starting at time t1. After a one cycle delay, the second and third waveforms 72 and 74 are transmitted. Three cycles later, the second and third waveforms 72 and 74 are no longer transmitted (zero value). The first and fourth waveforms 70 and 76 continue to contribute to the acoustic waveform 78 for one more cycle. Thus, the amplitude or envelope of the acoustic waveform 78 increases gradually from a zero value to a maximum value and then decreases gradually from the maximum value to the zero value.

Referring to FIGS. 6C and 6D, setting the number of cycles characteristic of the transmit waveforms is demonstrated for uni-polar transmit waveforms 80, 82, 84, and 86 to obtain an acoustic waveform, such as shown in FIG. 6B. By application of the transmit waveforms 80, 82, 84 and 86, the acoustic waveform is generated as if the waveform 88 is applied to the transducer. More or fewer transmit waveforms with more or fewer number of cycles may be used. Preferably, the number of cycles of the shorter duration transmit waveform or waveforms is a multiple of two cycles shorter than any longer duration waveform. The delay for transmission of the shorter duration transmit waveform or waveforms relative to the longer waveform or waveforms is preferably half the difference in duration between the waveforms. Other delays, including fractional delays, and combination of waveforms may be used. For example, three or more transmit waveforms corresponding to three or more numbers of cycles may be used. Thus, the amplitude or envelope of the acoustic waveform may increase or decrease more gradually.

Another characteristic of the transmit waveforms that is set for one transmit waveform relative to another to provide a desired acoustic waveform is the amplitude. The transmit beamformer 40 of FIG. 2 or any other transmit beamformers capable of producing a plurality of negative or positive amplitude levels produces an acoustic waveform with finer amplitude adjustment than the transmit waveforms. The amplitude levels associated with each waveform are set relative to another waveform to generate an acoustic waveform with a more gradually increasing or decreasing amplitude level or envelope. The amplitude, or shape amplitude, of one waveform set relative to another waveform is in addition to any apodization scaling or apodization amplitude settings.

For example and referring to FIG. 7, first and second transmit waveforms 100 and 102 are shown. In this example, the transmit waveforms 100 and 102 are associated with 7 possible amplitude levels (vertical axis of FIG. 7A). Other numbers of amplitude levels may be provided. At a time period t1, the amplitudes of the first and second transmit waveforms 100 and 102 are 2 and 1, respectively. After transmission, the waveforms corresponding to the transmit waveforms 100 and 102 sum in the acoustic domain to create an acoustic waveform. By application of the transmit waveforms 100 and 102, the acoustic waveform is generated as if the waveform 104 is applied to the transducer. At time t2, corresponding to time t1 of the application of the transmit waveforms 100 and 102 to the transducer, the transmit waveforms 100 and 102 effectively sum to an amplitude of 3. If the first and second transmit waveforms 100 and 102 have the same amplitude levels or are not set relative to each other, then the amplitude of the acoustic waveform is more limited. By setting the amplitude of the transmit waveforms 100 and 102 relative to each other, twice the number of amplitude levels associated with the acoustic waveform are possible, as represented by the waveform 104.

The characteristics discussed above are set for one or more transmit waveforms relative to one or more other transmit waveforms in combination or independently. For example, a first transmit waveform is delayed relative to a second transmit waveform. The first or second transmit waveform is also set to have a lesser number of cycles than the other transmit waveform. The amplitude of the first or second transmit waveform may also be set relative to the amplitude of the other transmit waveform. The number of cycles, amount of delay in addition to focusing delay and amplitude characteristics are set in any combination of two or all of the characteristics.

The examples discussed above and shown in FIGS. 3, 4 and 6 show four transmit waveforms or four channels. In each example, the two outside channel transmit similar waveforms, and the two inside channels transmit similar waveforms. Other groupings, including one or more transducer elements, may be used. Preferably, the transducer 16 (see FIG. 1) includes at least 64 transducer elements. One group of transmit waveforms is provided to every other transducer elements. A second group of transmit waveforms set relative to the first group of transmit waveforms is provided to the other transducer elements.

The examples discussed above and shown in FIGS. 3, 4, 5, and 6 represent application or transmission of the same uni-polar rectangular waveform or sinusoidal waveform to or from every transducer element. Different waveforms, such as uni-polar rectangular or bi-polar rectangular, may be applied to the transmitter. Further, any given channel may be used to transmit a waveform that is different than a waveform transmitted from another channel.

In one embodiment, the waveforms transmitted from each element in a transducer array are each delayed by ¼ of a cycle relative to the waveforms at adjacent elements. Every other waveform, such as from even numbered elements, is transmitted with a first ¼ cycle delay for reduction of transmitted harmonic energy, and the other waveforms, such as from odd numbered elements, are transmitted without the ¼ cycle delay. This delay profile is then altered for focusing, including steering. Thus, the ¼ cycle delay pattern is added to the focusing delay profile. In the acoustic domain, the transmitted waveforms sum so that the energy at the second harmonic destructively interferes and the energy at the fundamental constructively interferes.

Figure 8A:
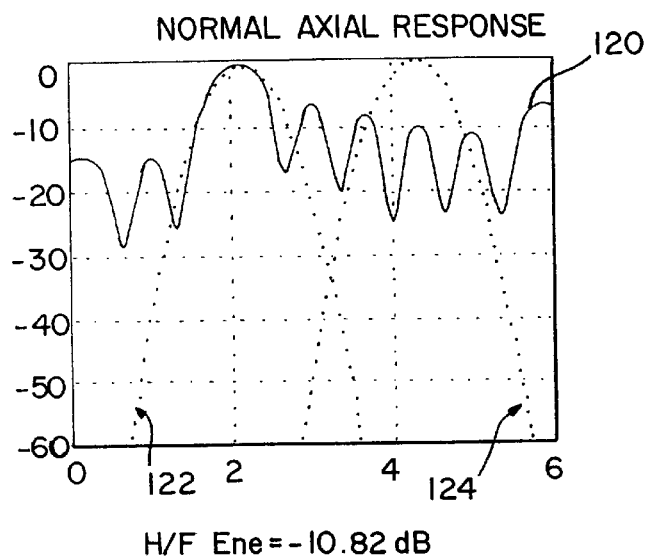
FIGS. 8A and 8B are graphical representations of a spectral response of a waveform in the acoustic domain.
Figure 8B:
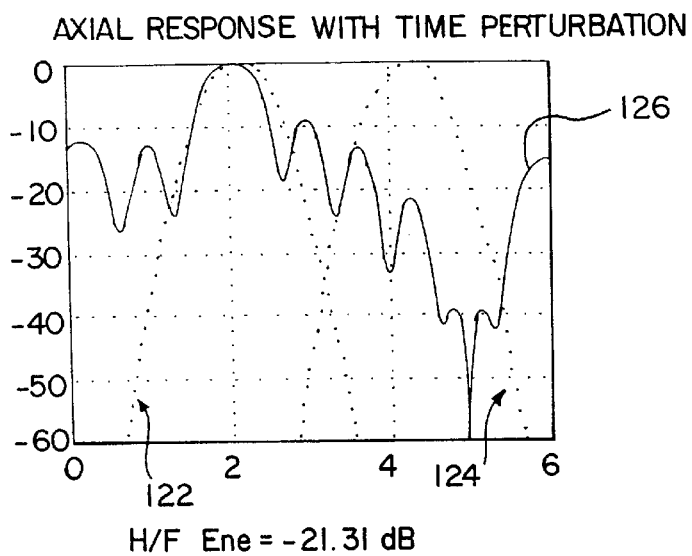

Referring to FIG. 8A, the spectral response at the focal point of waveforms transmitted without delaying waveforms relative to each other for reducing energy at the second harmonic is shown at 120. The spectral response 120 is associated with bi-polar square waves transmitted at a 2 MHz center frequency from a 64 element transducer. A representative fundamental frequency band centered at 2 MHz is shown as dashed line 122. A representative second harmonic frequency band centered at 4 MHz is shown as dashed line 124. Referring to FIG. 8B, the spectral response from transmitting the same waveforms with an every other element ¼ cycle delay is shown at 126. The energy in the second harmonic frequency band 124 is reduced as compared to the spectral response without the above discussed delay.

Instead of using a delay as discussed above, a phase difference between waveforms may be used, such as transmitting every other waveform with a 90 degree phase difference. Combinations of phasing and delay, or delays implemented through phase adjustment may also be used. I-II. Various characteristics of the null or reduction of energy in the harmonic frequency band may be changed by changing parameters or characteristics of the waveforms relative to other waveforms. For example, the bandwidth, frequency and/or roll-off associated with a null or reduction in energy may be changed. These characteristics of the reduction may be changed by setting different delay or phase, amplitude and cycle parameters of waveforms relative to other waveforms.

Figure 9:
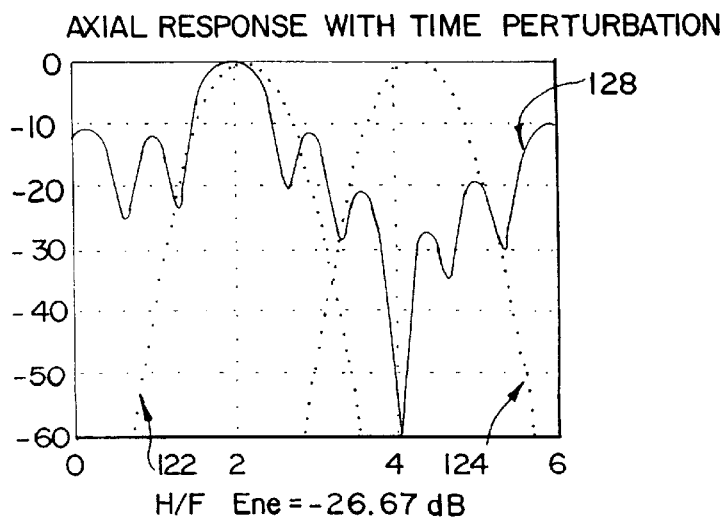
FIG. 9 is a graphical representation of a spectral response of a waveform in the acoustic domain.

In one embodiment, the position of the null or reduction of energy is changed. For example, the various delays of the waveforms associated with the spectral response shown in FIG. 8B are altered to move the null from about 5 MHz to about 4 MHz as shown by the spectral response 128 in FIG. 9. To obtain the spectral response 128, most of the waveforms are delayed by ¼ cycle relative to each other as discussed above. However, every eighth waveform is additionally delayed by 0.1875 cycles (67.5 degrees) relative to waveforms transmitted from adjacent elements. Other additional or reduced delays with other combinations or groupings of waveforms or elements may be used to vary characteristics of the spectral response. Furthermore, additional or reduced delays, combinations or groupings of waveforms or elements, amplitudes associated with each waveform and the number of cycles may be independently changed to alter characteristics of the spectral response.

In one embodiment, the groupings of waveforms or elements comprise unequal groupings of elements, such as 63 elements of a 128 element array in one grouping and 65 elements in the other grouping or groupings of 43, 43 and 42 elements. One or more groupings comprise at least two adjacent transducer elements. In an alternative embodiment, the groupings comprise equal groupings of elements, such as transmitting waveforms with two different parameters from every other element respectively. In yet other alternative embodiment, one or more groupings comprise at least two adjacent transducer elements. For example, groups of four or more adjacent elements are used to transmit the same waveform, and adjacent groupings of elements are used to transmit waveforms with at least one different parameter. Various combinations of the groupings may be used.

In another alternative embodiment, setting the parameters or characteristics of the waveforms relative to other waveforms for reduced harmonic transmission is used for a sub-set of the waveforms transmitted to form a transmit beam. For example, additional delay (or phase), amplitude or number of cycles are provided for some waveforms associated with a center group of elements in the array. Waveforms transmitted from elements at the sides of the array are transmitted and focused in a conventional manner. Groupings of elements associated with different parts of the array may be used, such as non-symmetrical grouping (e.g., elements 1–5 and 65–128 for conventional delay profile and elements 6–64 for delays or phasing in addition to focusing delays or phasing). More or fewer groupings may also be used.

In yet another alternative embodiment, transmit beams formed as discussed above are used for less than all the scan lines within an image. For example, conventional transmit beams are transmitted for scan lines at the edge of an image region, and transmit beams formed as discussed above are transmitted for scan lines at the center of the image region. Different, more or fewer groupings of conventional and other transmit beams and associated scan lines may be used. Furthermore, the parameters of the waveforms relative to other waveforms may be changed as a function of the scan line position or focal depth.

In a preferred embodiment of this alternative, an aperture size for transmitting the waveforms with different parameters to generate a transmit beam changes as a function of an angle of the scan line. For example, waveforms characterized by different delays or phases in addition to focusing delays are transmitted in one portion of an active aperture, and waveforms characterized by a conventional delay or phase profile are transmitted from another portion of the active aperture.

Figure 10:
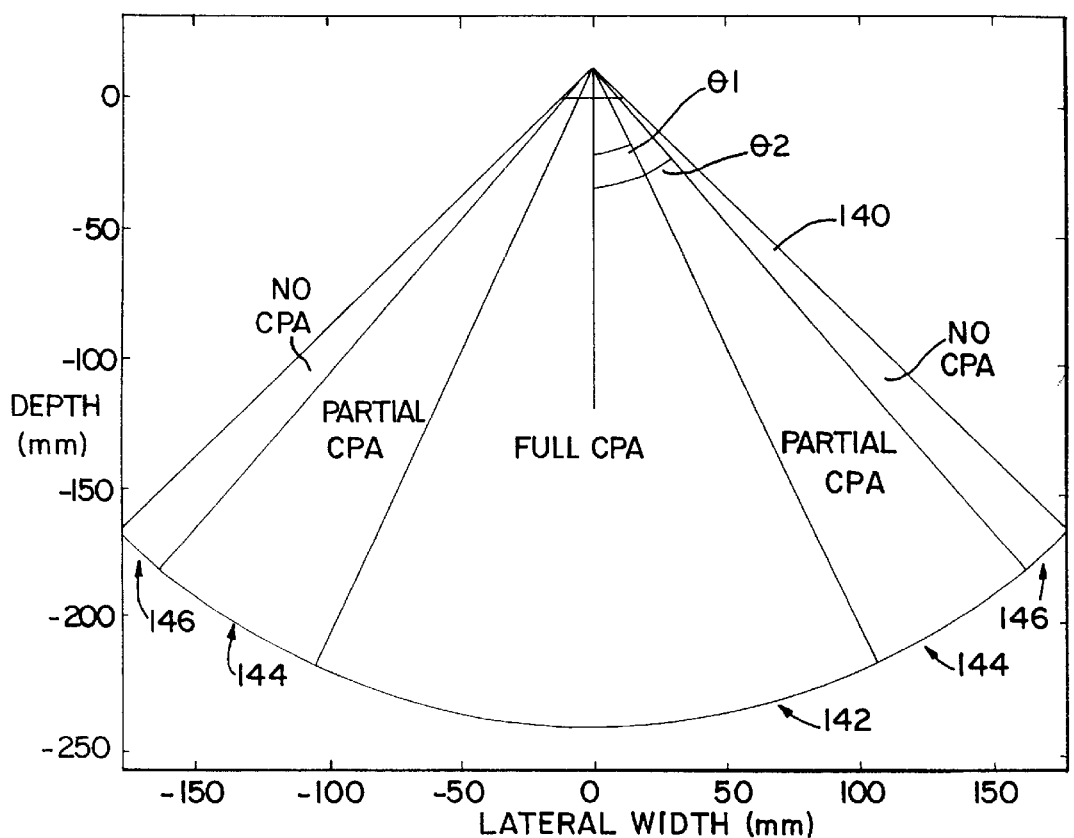
FIG. 10 is a graphical representation of an image divided by scan line angle.

As shown in FIG. 10, an image region 140 is divided into various portions, such as center portion 142, intermediate portions 144 and edge portions 146 as a function of scan line angle or position. For the center portion 142, different delays or phases, such as alternating the delays or phases by 90 degrees, are used in addition to focusing delays for each waveform across the entire aperture, such as 128 elements. Other delay or phase profiles may be used. In the sector image format shown, the center portion comprises scan lines associated with angles less than a first angle from the center line, such as 20 degrees.

For the intermediate portions 144, different delays or phases, such as alternating the delays or phases by 90 degrees, are used for only a portion of the aperture. For example, waveforms characterized by different delays or phases are applied to elements 70 through 125 of a 128 element transducer. Conventional waveforms (i.e., without different delays or phases in addition to focusing) are applied to the remainder of the aperture, such as elements 25-through 69 and 126–128. Different portions of the aperture may be used for different delays or phasing in addition to focusing delays or phasing, such as non-contiguous, centered, or symmetrical portions of the aperture. The aperture associated with scan lines in the intermediate portions 144 may comprise a subset of all possible elements. The intermediate portions 144 comprise scan lines with angles greater than the first angle and less than a second angle, such as from 20 degrees to 35 degrees.

For the edge portions 146, conventional waveforms (i.e. without different delays or phases) are applied across the entire aperture used for transmitting beams. In alternative embodiments, the portions 142, 144, and 146 comprise different scan line angles. Different aperture sizes may be used for any of the portions 142,144 and 146.

The aperture may also change as function of the scan line angle within one or more of the portions 142, 144 and 146 or regardless of any division within the image region 140. The aperture for applying differing delays or phases in addition to focusing delays is changed depending on the scan line angle. Preferably, as the angle increases away from the center scan line, the aperture for applying differing delays or phases is decreased. In alternative embodiments, this aperture is constant regardless of scan line angle or changes independently of scan line angle.

Figure 11A:
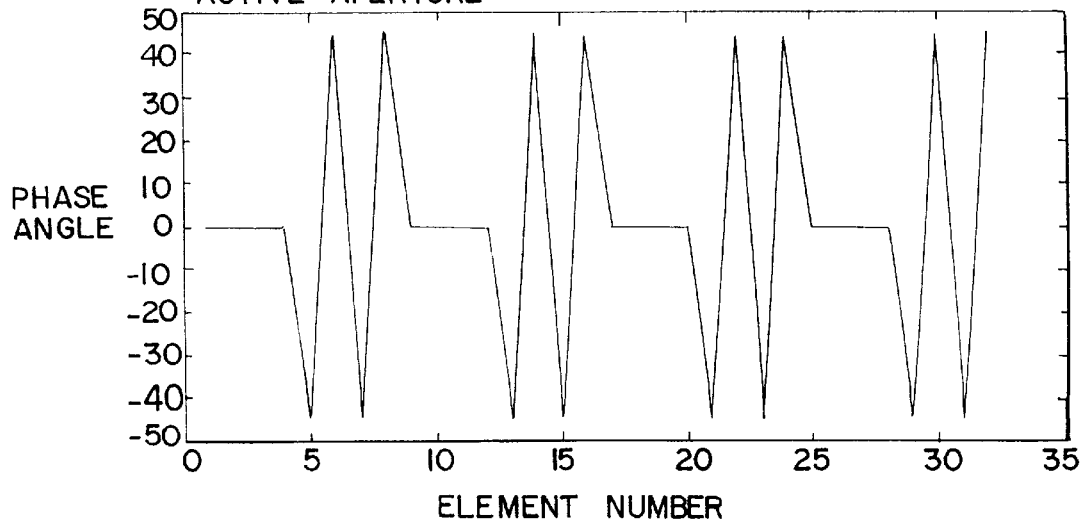
FIGS. 11A–C are graphical representations of phase or delay profiles.
Figure 11B:
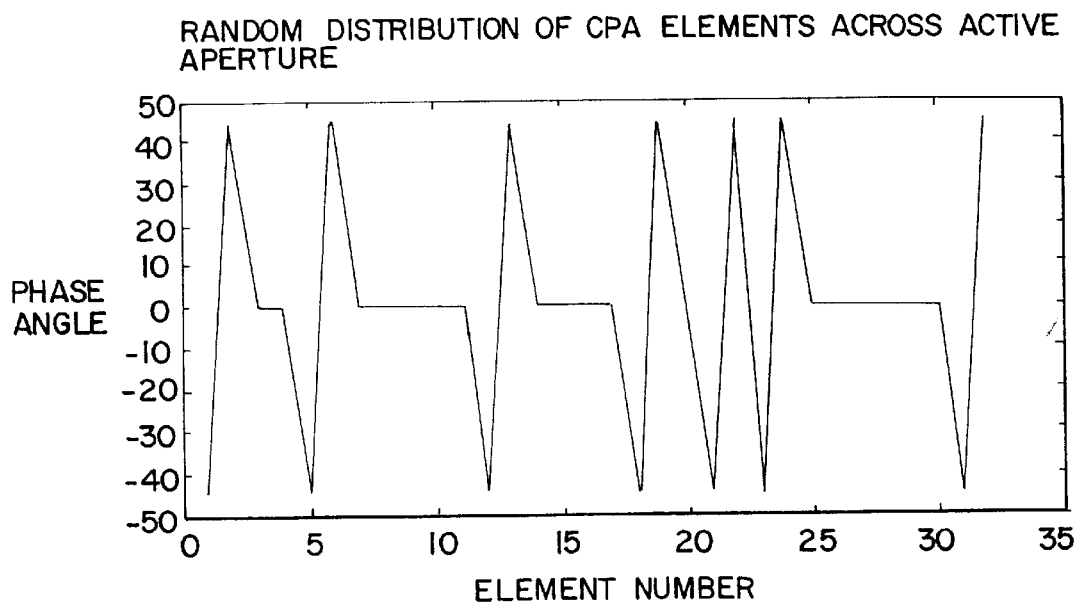
Figure 11C:
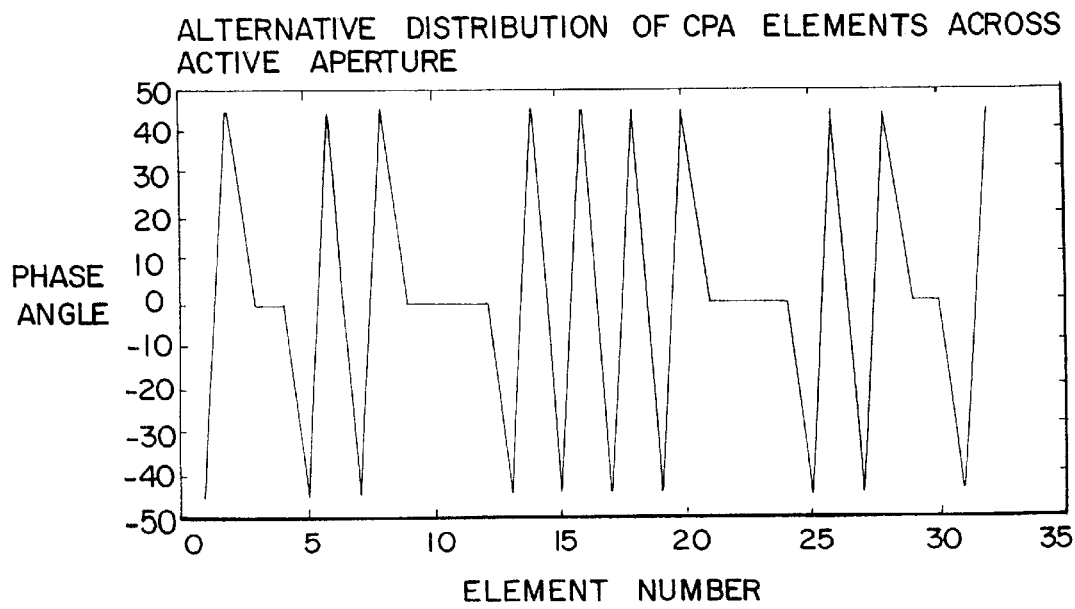
Figure 12:
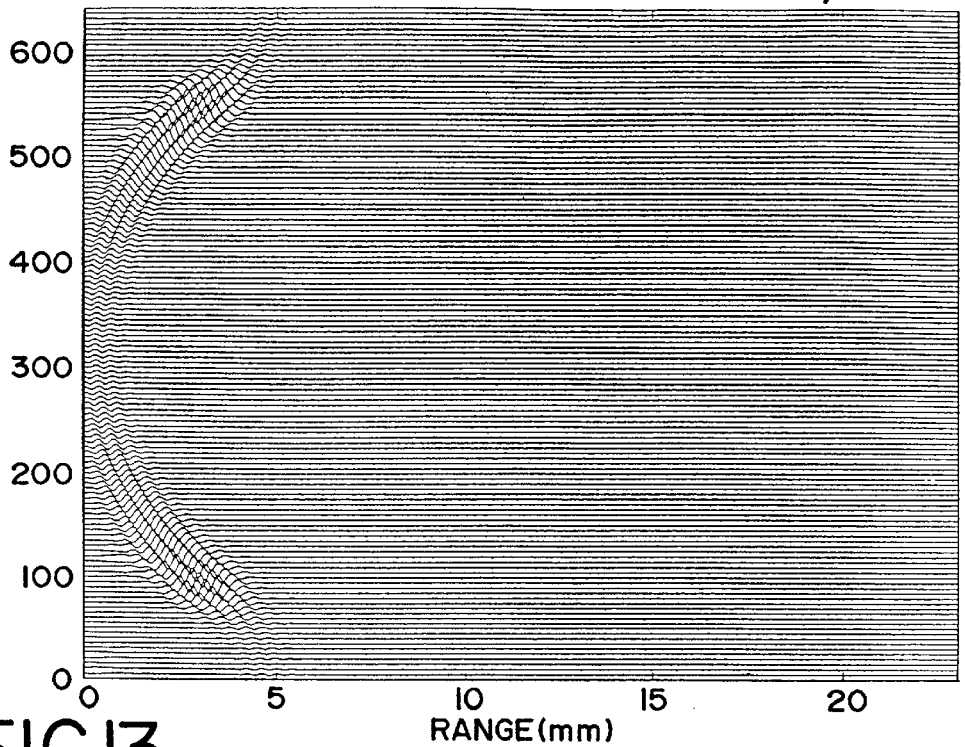
Figure 13:
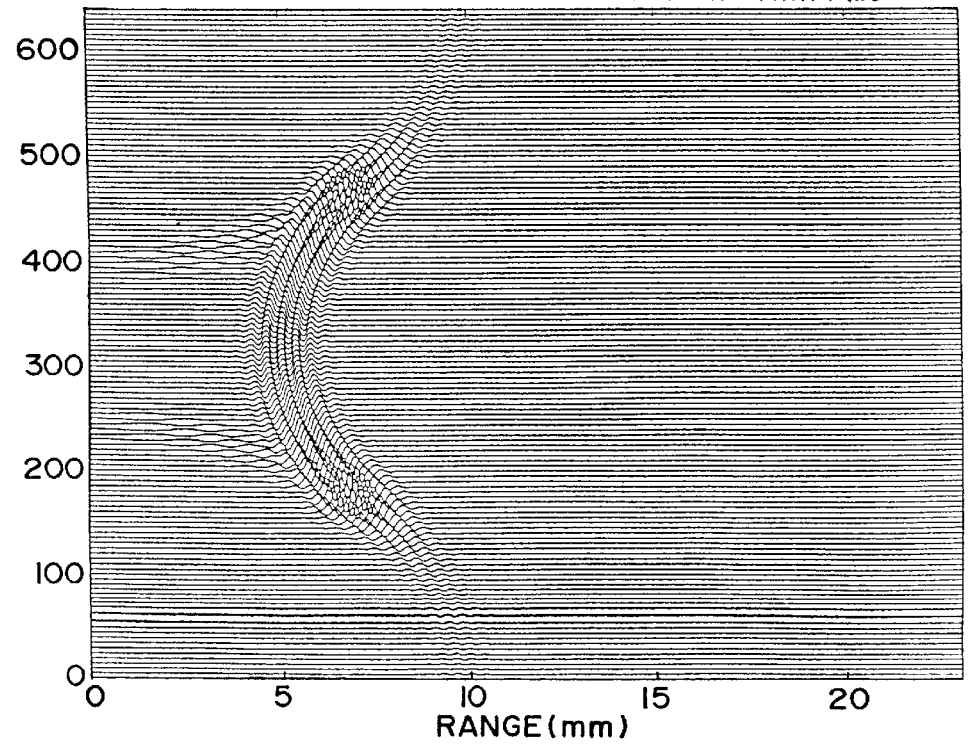
Figure 16:
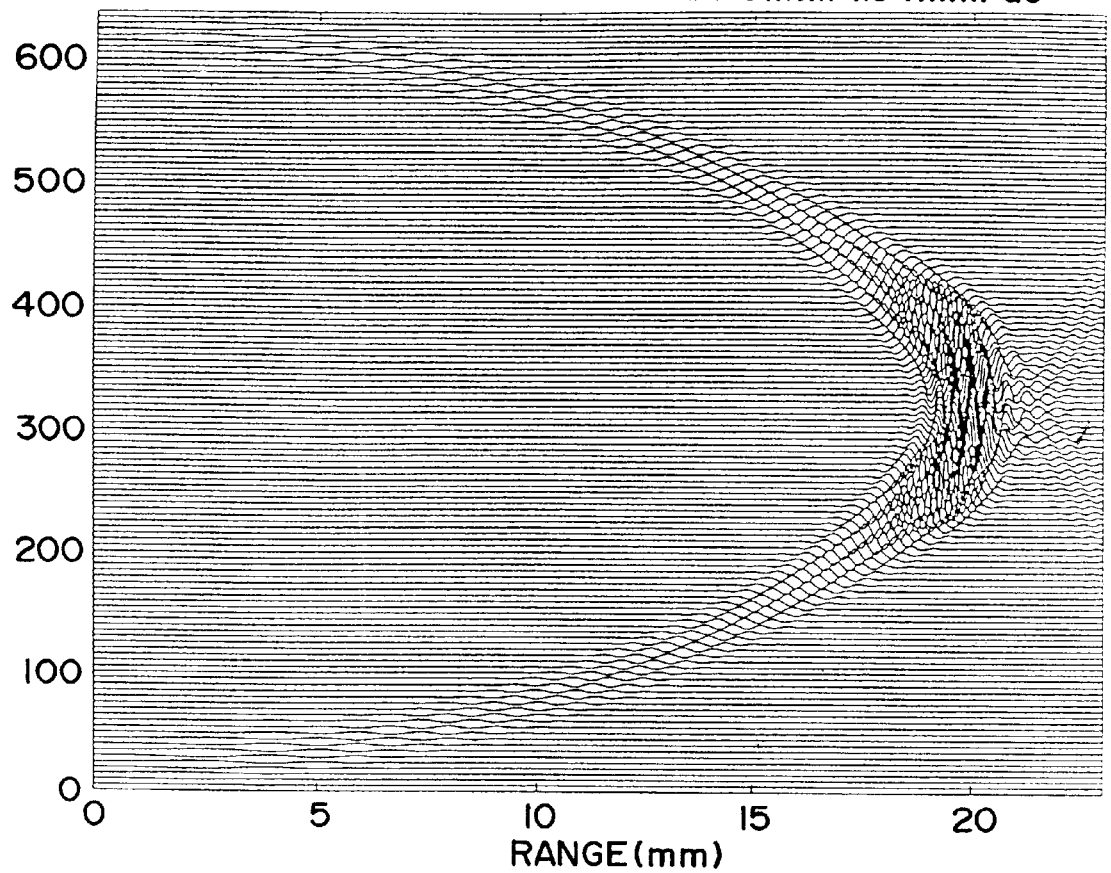
Figure 17:
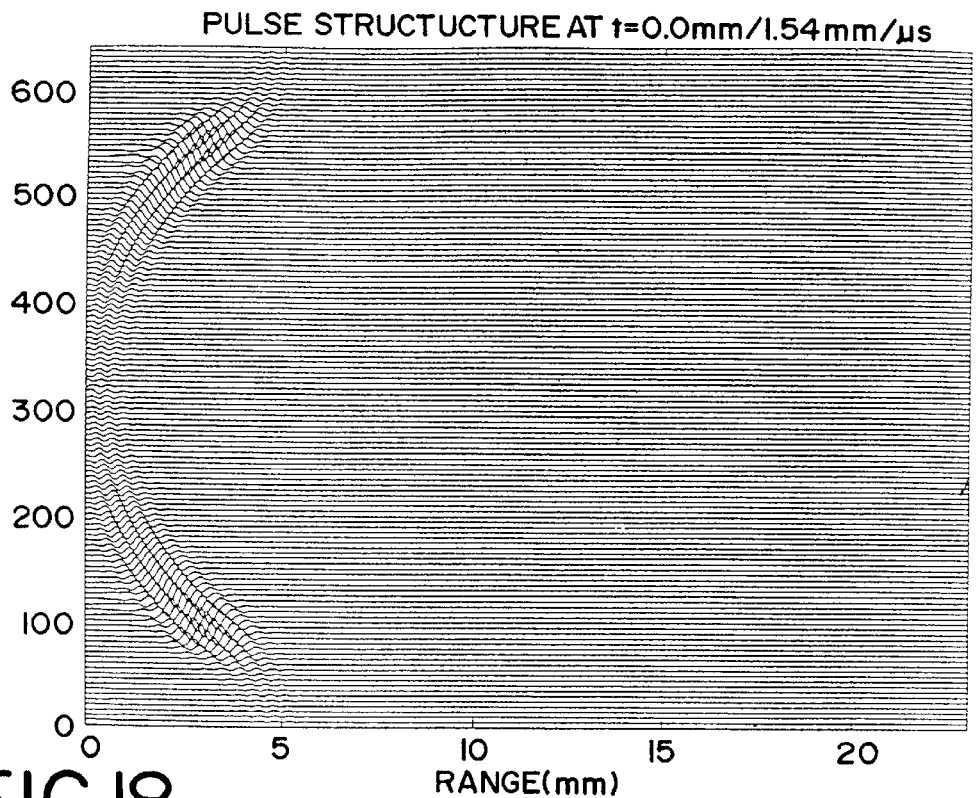
FIGS. 17 through 21 are diagrams illustrating a beam structure of a fundamental pulse for a split-phase aperture embodiment of this invention.
Figure 18:
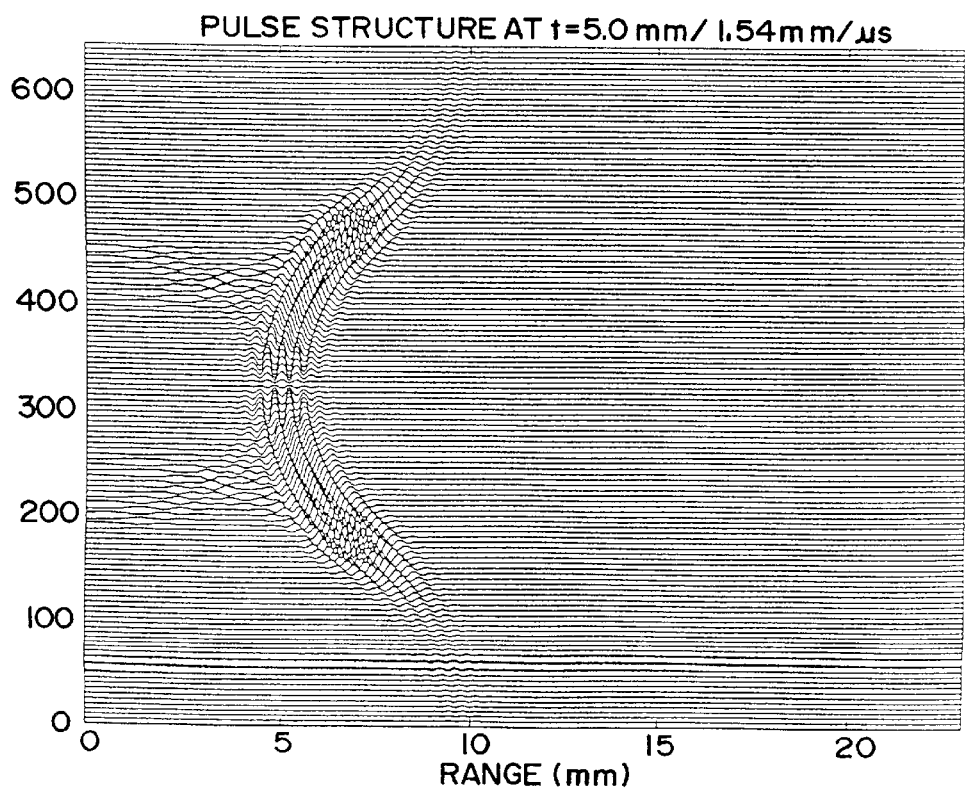
Figure 19:
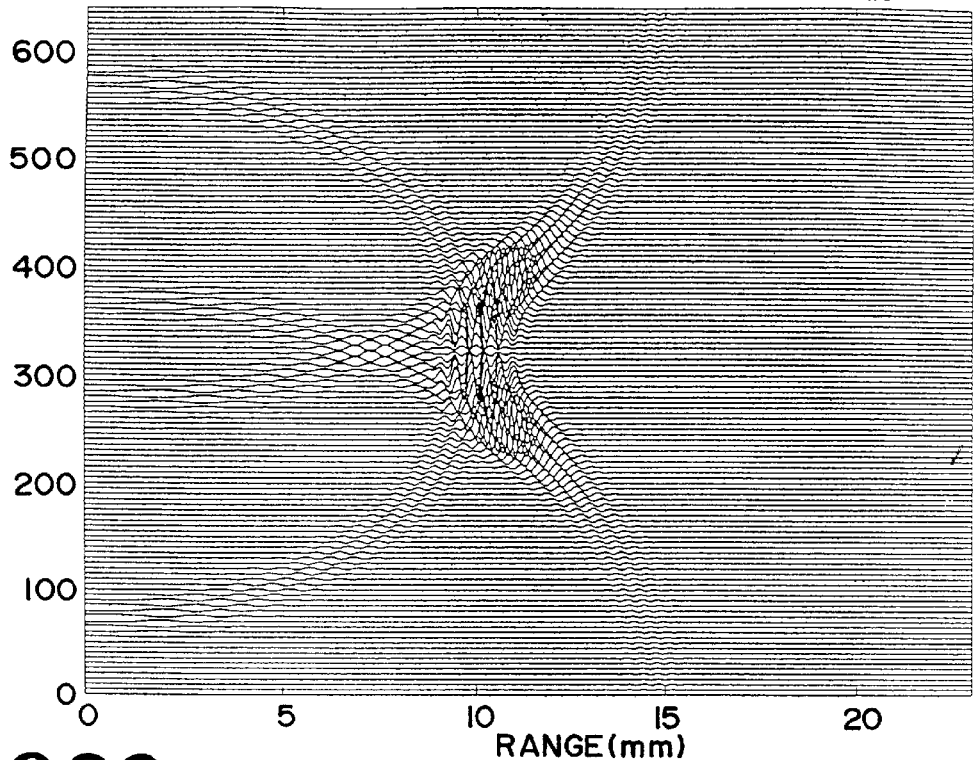
Figure 20:
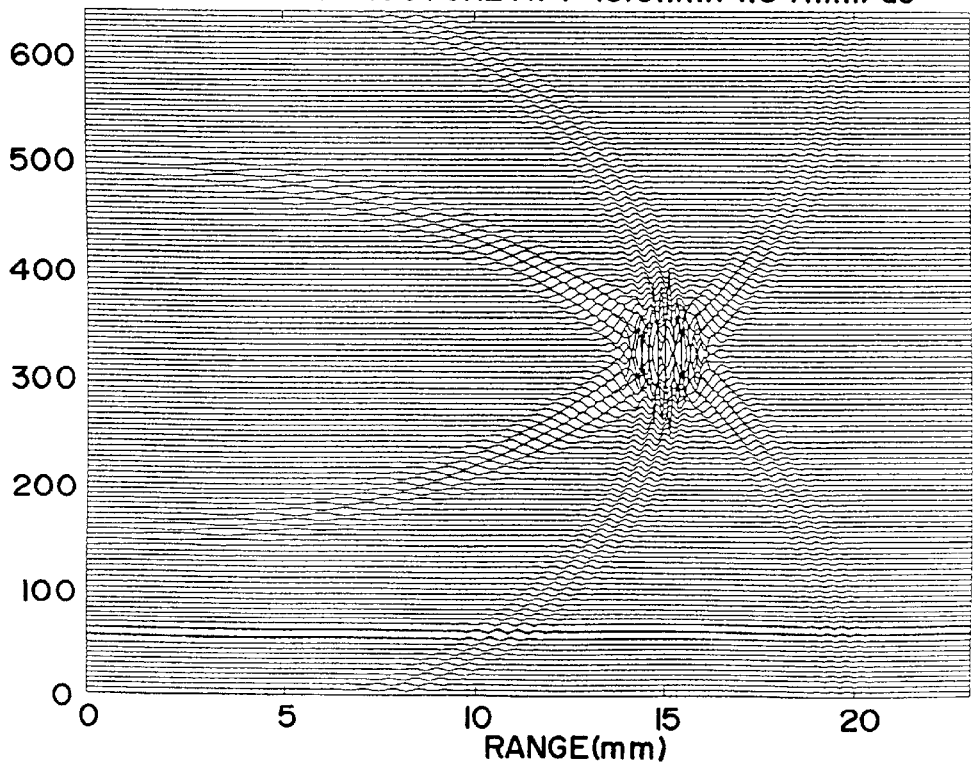
Figure 21:
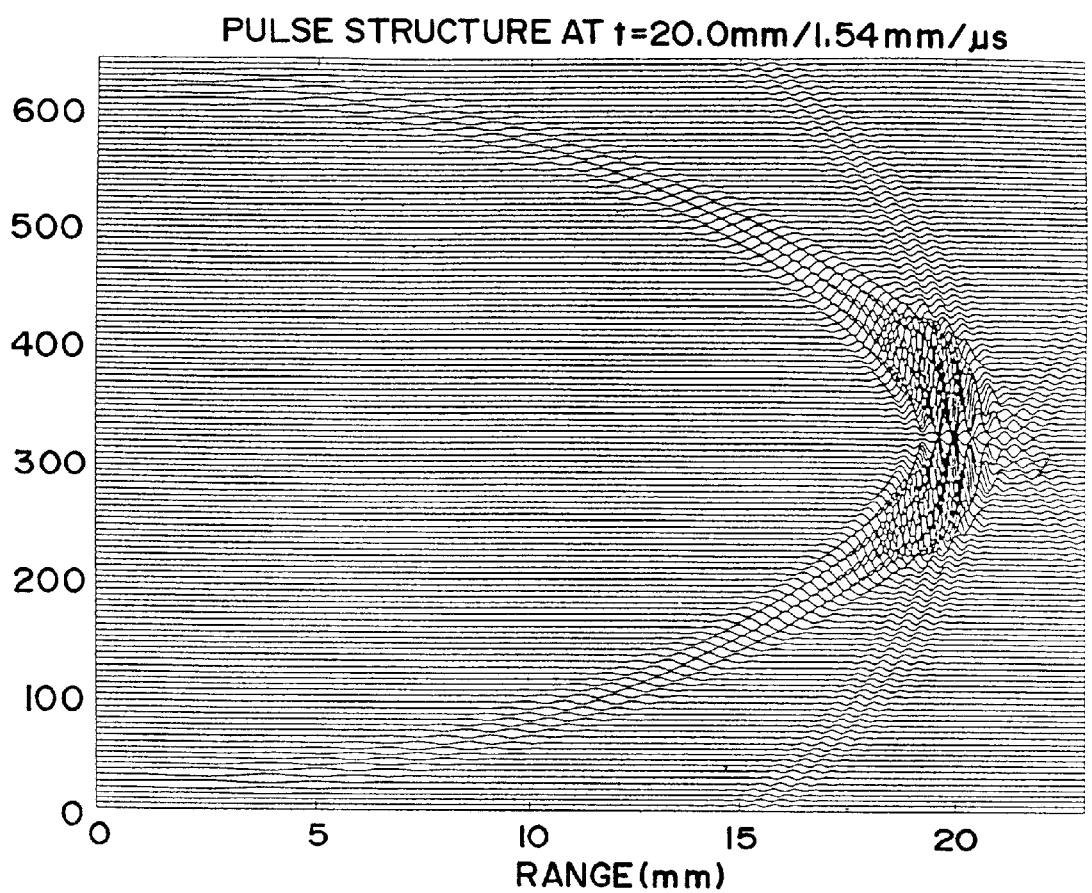

In alternative embodiments, each scan line is associated with one of two or more focal depths. The use of waveforms characterized by different delays or phases in addition to focusing delays (e.g. alternating phases) may vary as a function of focal depth. The aperture changes as a function of focal depth. The aperture for applying such waveforms may be centered or off-set within the active aperture. Furthermore, the aperture for applying such waveforms may comprise two or more separate sub-apertures within the active aperture. For example, FIGS. 11A–C represent various phase angles applied across an active aperture. FIG. 11A represents a periodic phase profile. FIG. 11B represents a random distribution of phase across the active aperture. FIG. 11C represents a alternative distribution of phase.

In addition to setting one or more characteristics of the one transmit waveform relative to another transmit waveform, the transmit waveforms may also be shaped individually. For example, the transmit waveform is a uni-polar waveform or a bi-polar rectangular waveform. The amplitude of each transmit waveform is shaped to gradually rise to a maximum value and gradually decrease from the maximum value. Each transmit waveform characterized by modulating a carrier waveform with an envelope waveform. Alternatively and with respect to transmitting a uni-polar waveform, a shaped low pass off-set waveform with a gradually increasing and decreasing amplitude is summed with a bi-polar waveform in real time or off-line. The shaping of the amplitude of the transmit waveform to reduce energies associated with harmonic frequencies is discussed in U.S. application No. 09/338,319 for Ultrasound Imaging Method And System For Transmit Signal Generation For An Ultrasonic Imaging System Capable Of Harmonic Imaging, assigned to the assignee of the present invention and filed concurrently herewith, the disclosure of which is hereby incorporated by reference.

As an alternative embodiment, one or more filters are added to the transmit beamformer 40 of FIG. 2. A filter, such as an analog, low pass or a notch filter, filters the output of the signal generator. The output of the waveform generator 162 is any of the various waveforms discussed above, such as the bi-polar waveforms, or other waveforms. The filter reduces the transmitted energy associated with various harmonic frequencies, such as at least by 30 dB with respect to the fundamental frequencies. Thus, the generated waveform as discussed above and the filter, in combination, reduce the transmitted energy associated with harmonic frequencies. As a further alternative, the filter, such as a low pass analog filter, filters the output of the DAC or the amplifier. The filtering of the waveform to reduce energies associated with harmonic frequencies is discussed in U.S. application No. 08/893,288 for Ultrasonic Contrast Agent Imaging System and Method (a continuation-in-part of U.S. application Ser. No. 08/642,528), assigned to the assignee of the present invention and filed concurrently herewith, the disclosure of which is hereby incorporated by reference.

As yet another alternative embodiment, the transmit waveforms discussed above are pulse width modulated. As disclosed in U.S. application No. 08/893,287 for Ultrasound Imaging Method and Apparatus For Generating Pulse Width Modulated Waveforms With Reduced Harmonic Response, assigned to the assignee of the present invention and filed concurrently herewith, the disclosure of which is hereby incorporated by reference, the duration of each pulse within a burst is selected to reduce the energy transmitted at harmonic frequencies. In particular, the duration of one or more pulses is different than other pulses within the burst. Preferably, the width of the pulses within the burst gradually increase and then decrease, but other duration patterns may be used. To generate pulses with different widths, the sequence of values in the delay words 50 (see FIG. 2) enable each pulse at a set duration. Alternatively, the waveform generator, based on control signals or storing the waveform in memory, generates the waveform after the entire burst is enabled by the appropriate delay word 50.

Any of the various alternatives discussed above, such as pulse width modulation, filtering, generation of waveforms with multiple amplitudes and summation of waveforms in the acoustic domain may be used in combination. The combination may include more than two of the alternatives discussed above.

It should be understood that many changes and modifications can be made to the embodiments described above. For example, different ultrasound systems with different levels of programmability may be used. Different transducers and system configurations may also be used. Many of the various processes discussed above may be analog or digital processes. It is therefore intended that the foregoing detailed description be understood as an illustration of the presently preferred embodiments of the invention, and not as a definition of the invention. It is only the following claims, including all equivalents, that are intended to define the scope of the invention.

II. This is a description of medical ultrasonic diagnostic imaging systems and methods that result in improvements in harmonic ultrasound imaging. Two different classes of embodiments are described that apply to two different intended target applications. The first is intended to improve the performance of THI (tissue harmonic imaging), and the second is intended to improve HCAI (harmonic contrast agent imaging).

In both THI and HCAI, acoustic pulses that occupy some fundamental frequency band are launched from the ultrasound transducer, and the resultant backscattered signal is received. This received signal generally contains a much broader range of frequencies than that which was launched. Most notably, there is generally energy in the second harmonic band, which is the band of frequencies that are double those that occupy the fundamental band. The energy in the second harmonic frequency band comes about as a result of a number of different physical mechanisms, but most notable are two. The first is classic nonlinear acoustic propagation distortion. Second harmonic energy is generated and gradually accumulates as the fundamental pulse propagates from the probe out towards the transmit focus. The resultant second harmonic signal is referred to as the tissue harmonic signal, and is the signal used for imaging in THI. The second physical mechanism is nonlinear scattering. Harmonic distortion occurs during the (highly nonlinear) backscatter of the fundamental from the contrast agent bubble. The resultant second harmonic signal is referred to as the contrast harmonic signal, and is the signal of interest in harmonic contrast agent imaging.

One of the great difficulties in THI is the extraction of the relatively small tissue harmonic signal from the total signal, which is composed primarily of the fundamental. The embodiments of the invention that address THI are intended to suppress the fundamental signal level with either an increase in the THI second harmonic signal level or at least minimal suppression of that signal. In a somewhat similar vein, one considerable potential improvement in contrast agent imaging is the suppression of the THI signal (which competes with the contrast agent signal) relative to the contrast agent signal. The embodiments of the invention that address contrast agent imaging are intended to do exactly that. They suppress the THI signal with an increase (or at least minimal suppression) of the second harmonic signal that arises from the contrast agent. The best mode of operation for each of these embodiments is described as follows.

Tissue Harmonic Imaging

For THI imaging, the usual transmit aperture is modified with an element-dependent phase shift. One part of the transmit aperture is advanced in phase by ¼ of a fundamental cycle, and another part is retarded in phase by the same amount (see FIG. 23a). For example, two subapertures are driven with transmit waveforms that are 180 degrees out of phase with one another. Of course, such a 180 degree phase shift can be obtained with other asymmetrical phase shifts to the subapertures (e.g. (+180°, 0°), (−180°, 0°), (+45°, −135°), etc.). The resultant fundamental field bears a fairly large degree of qualitative similarity to that associated with the unmodified transmit aperture, except that the field is antisymmetric with respect to the beam axis (in the imaging plane), and therefore has a null along the beam axis.

Figures 23A, 23B, 23C:
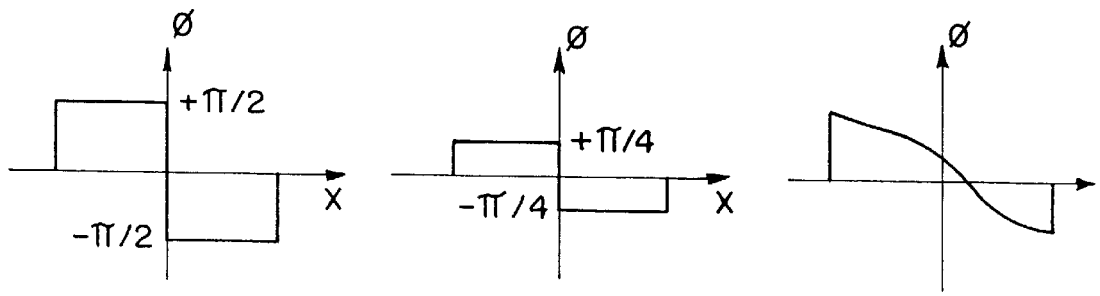
FIGS. 23a, 23b and 23c are phase function diagrams of three embodiments of this invention, showing phase shift as a function of position along the azimuthal (X) direction of a phased array transducer.

FIGS. 12–16 show the beam structure of the fundamental pulse for the conventional, unmodified aperture, and FIGS. 17–21 show the same sequence for the corresponding split-phase aperture of FIG. 23a. Note that the beam structures are very similar except for (1) the axial null, and (2) the phase reversal of the left and right halves of the field in the case of the split-phase aperture.

Figure 22:
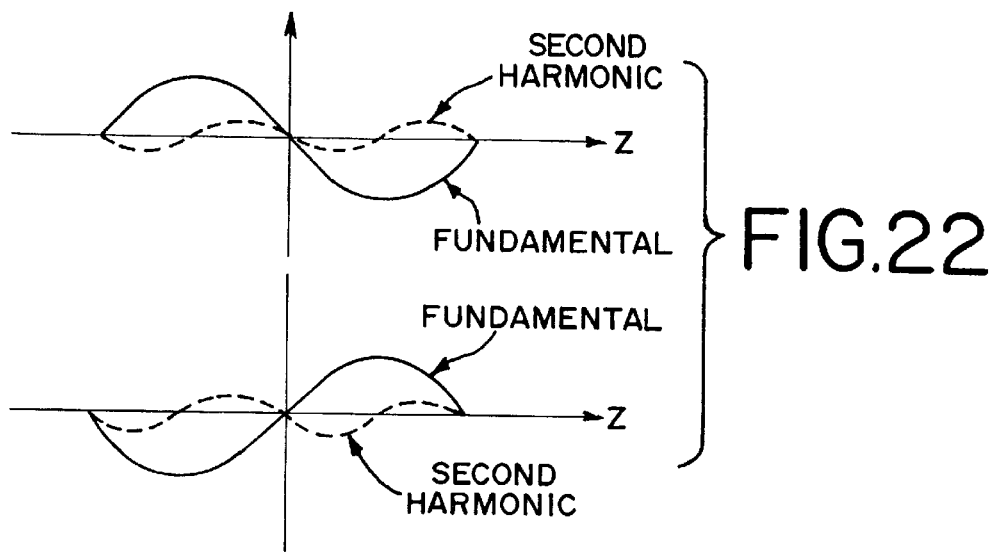
FIG. 22 is a waveform diagram illustrating that a 180 degree phase shift inverts a fundamental waveform but not a second harmonic waveform.

The generation of a second harmonic field by this fundamental field also bears a similarity to the second harmonic field generated when using the unmodified aperture. In fact, the degree of similarity is greater than in the case of the fundamental field. Where the fundamental field is antisymmetric with respect to the beam axis, the second harmonic field is symmetric (inverting the fundamental phase inverts the phase of only the odd harmonic frequency components; even harmonic components are left unchanged—see the example shown in FIG. 22). Along the beam axis, where the fundamental field has a null, the generation of second harmonic is reduced. Elsewhere in the field, however, the second harmonic field is relatively unaffected. What's more, the depression in the second harmonic field level along the beam axis tends to stitch itself together quite quickly as the phase-aligned waves on either side of the beam axis diffract into one another.

The result, particularly away from the transducer face, is a second harmonic field that is quite similar to that which is found using the unmodified transmit aperture, but a fundamental field that has a null on the beam axis. Because the receive beamformation selects the backscattered signal that arises along the beam axis, the ultrasound line data has suppressed fundamental levels relative to the second harmonic levels.

Harmonic Contrast Agent Imaging

The best mode of operation for the case of harmonic contrast agent imaging is very similar to that described above for THI, but the phase of one transmit subaperture is advanced by ⅛ of a fundamental cycle (as opposed to ¼ in the THI case), and another subaperture is retarded by ⅛ cycle (see FIG. 23b). As before, other asymmetrical phase shifts or delays can be used to achieve the desired phase difference of pi/2. The resultant fundamental field is somewhat distorted by such aperture phasing, but the fundamental field level on axis is typically only mildly decreased (by about 3 dB). The second harmonic field generated by such a fundamental field, however, is antisymmetric with respect to the beam axis. Much like the fundamental field described in the THI section above, this tissue second harmonic field has a null on the beam axis (see FIGS. 17–21).

Again, because the receive beam formation selects backscattered signals that originate very near the beam axis, there is little tissue second harmonic signal present in the ultrasound line data. The fundamental field levels on axis remain sufficiently strong, however, to excite the generation of a contrast agent second harmonic field. If the level of the second harmonic signal due to the contrast agent relative to the THI signal is compared for the split-phase aperture case and the unmodified aperture case, it is found that the split-phase aperture case has a larger ratio. In other words, the competing (problematic) THI signal is reduced compared to the desired (contrast agent) signal. This is the advantage of split-phase HCAI over usual HCAI.

Examples of Implementation

Figure 24:
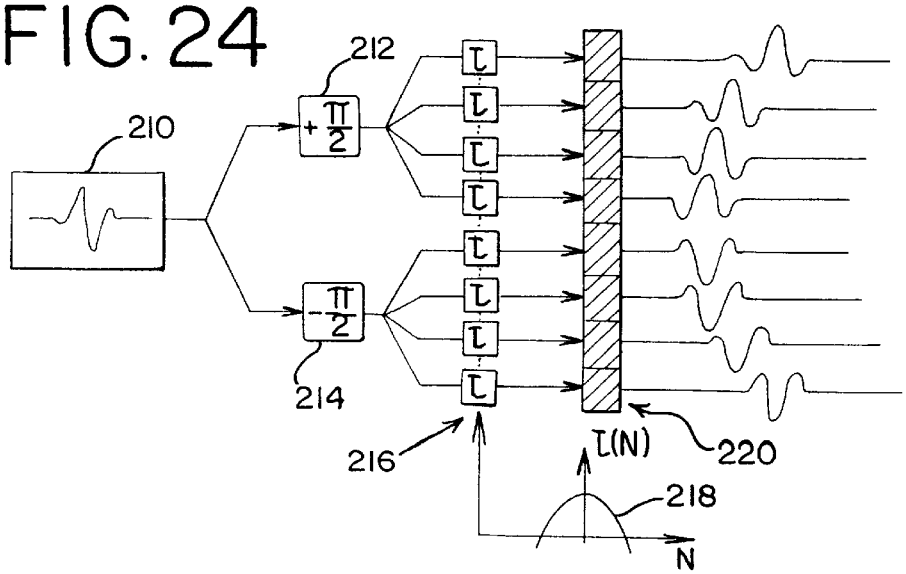
FIGS. 24, 25 and 26 are block diagrams of three alternative embodiments of this invention.

An example of a particularly simple implementation of this invention is illustrated schematically in FIG. 24. A pulse generator 210 generates a pulse and sends it to a pair of parallel phase shifters 212, 214. The phase shifters are used to apply a generally different phase shift to the two signals, and the resultant signals are sent to the left and right halves of a bank of delays 216. In FIG. 24, the phase shifts are shown to be +/−pi/2, or a differential phase shift of pi. In other words, the two resultant signals are 180 degrees out of phase with one another, which is the phase difference of interest for the embodiment of the invention intended for THI. If instead we were interested in HCAI, the shifts would be +/−pi/4, or any other combination of phases that results in a phase difference of pi/2 (90 degrees).

The delays are set according to a delay profile 218, such as is well known in the art, that causes focusing at a depth of interest. The signals are then sent to the transducer 220. Note that in a practical ultrasound system, there would be many intervening stages, such as transmit amplification stages, that are left out of this schematic overview as they are not pertinent in the description of the invention.

The resulting acoustic field bears some similarity to that which is typical of a conventional diagnostic ultrasound system, except that half of the transmitted field is phase shifted with respect to the other half.

Figure 25:
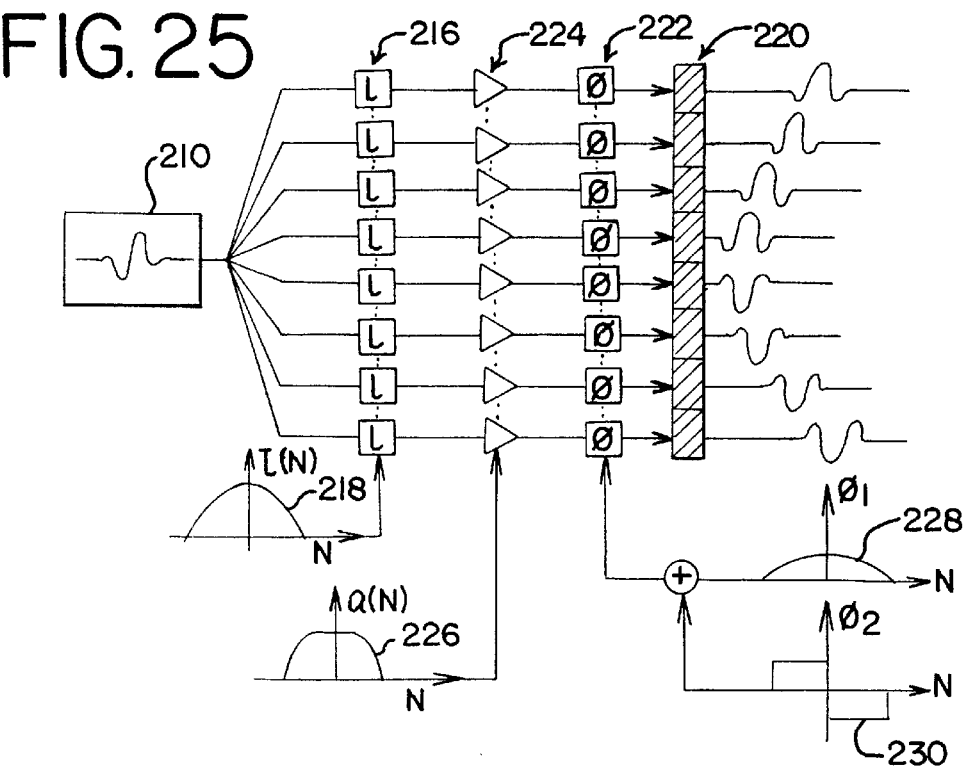

A somewhat more complicated example of the implementation of the invention, but one that is particularly relevant to current ultrasound system architecture, is shown in FIG. 25. In this case, the phase shifts that are applied to each subaperture are applied in a bank of element-by-element phase shifters 222. Such a bank of phase shifters 222 exists, for example, in the current Sequoia ultrasound system sold by Acuson Corporation. These phase shifters are used in conjunction with the delays to cause focusing of the transmitted ultrasound beam. In the context of such a system architecture, the subaperture phase shifts that are of interest here may simply be added to those that are imposed for the purpose of focusing.

Again a pulse generator 210 generates a pulse that is then sent to a number of delay lines that apply the focusing delays to each channel. Apodizing amplifiers 224 similarly apply gain to each channel as specified in an apodization profile 226. The signals then go to the phase shifters 222, which shift the phase of each channel by an amount that is the sum of (1), the focusing phase profile 228 and (2), the additional subaperture phase profile 230 that is of interest here. The signals are then sent to the transducer 220 and the result is again a focusing ultrasound beam with subaperture phase difference across the beam.

Figure 26:
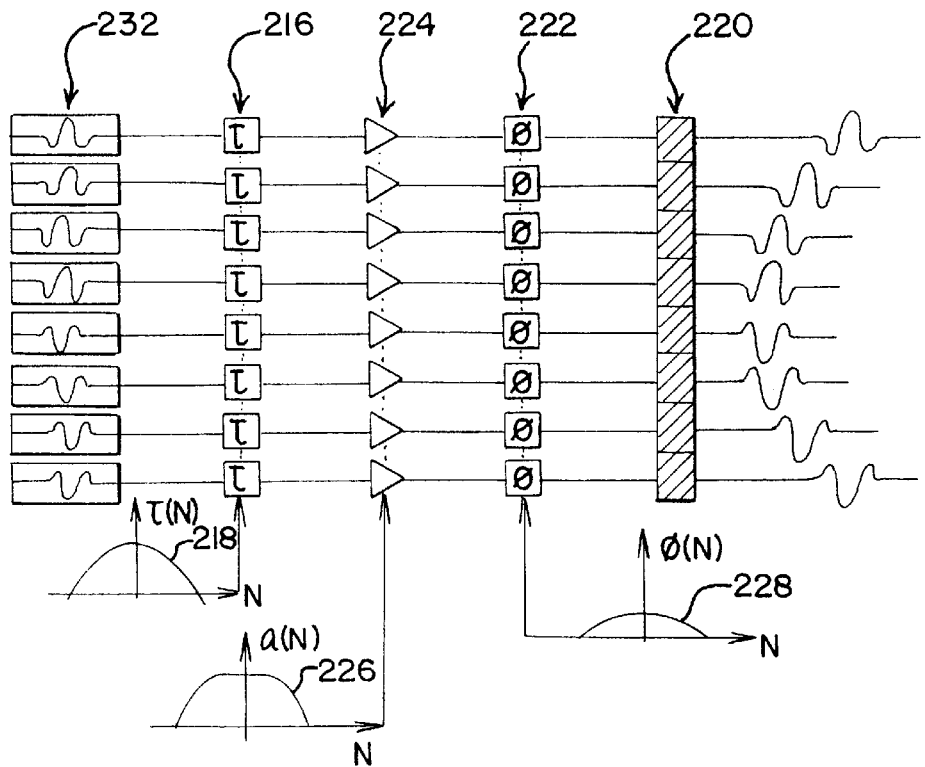

Again, these examples of implementation are presented in a high level, block-diagram form for clarity of presentation. The important feature is the application of a substantially different phase to different groups of elements in the transmit aperture, regardless of where the phase shifts are imposed. FIG. 26, for example, shows a schematic view of an ultrasound system that is similar to that shown in FIG. 25 except that it has a separate pulse generator 232 for each transmit channel. In such a system, the subaperture phase difference may be applied in the focusing phase shifters 222, as it was in the example of FIG. 25, or it may be applied in the pulse generators 232. That is, the pulse generators 232 themselves may be programmed to generate pulses that, before the focusing delays and phase shifts are applied, have the desired subaperture phase difference of interest here. This is the case shown schematically in FIG. 26.

In another variant, the invention is implemented using delays instead of phase shifts. Consider the case in which the phase function to be applied (such as one of those shown in FIGS. 23a, 23b, 23c) causes a particular system channel to have a phase shift of P radians imposed. An equivalent time delay of P*T/(2*pi), where T is roughly the period of the pulse carrier, can be applied in place of the phase shift. Likewise a combination of a phase shift and a time delay can be used. If P is the desired phase shift, then a phase shift of P1, in conjunction with a delay of (P−P1)*T/(2*pi), may be used.

Other variants are also possible. A system that is capable of transmitting multiple transmit beams simultaneously may apply the split-phasing to one, more than one, or all of the transmit beams. A system that makes use of sequential transmit focus modes, in which the image is formed using transmitted beams that are focused at more than one depth, may make use of the split-phasing for one, more than one, or all of the transmit focus depths. Similarly split-phasing may be made use of preferentially in different parts of the image along the azimuth. For example, split-phasing may be used during acquisition of data for a center part of the imaging plane and not for the edges, or vice-versa. The apodization profiles may be substantially different in split-phase operation than they are in normal operation. For example, there may be substantial dips in the apodization profile that would not usually be considered useful in conventional imaging. Likewise, delay profiles other than the usual hyperbolic delay profiles may be used. Examples of such delay profiles include line-focus or axicon delay profiles, which are used to extend the depth of focus.

More General Forms of the Invention

More generally, embodiments of this invention add a phase profile to a standard transmit aperture. This standard aperture may already have some phase profile for the purpose of focusing and/or beam steering. The added phase profile is not symmetric (i.e., is either asymmetric or antisymmetric) and is selected for the purpose of changing the balance of fundamental and second harmonic field levels along the ultrasound line (see FIG. 23c). Note that these phase profiles may, in cases such as the HCAI case described above, cause some steering of the transmit beam. The receive beam, however, remains focused along the ultrasound line and is not necessarily modified to steer along the fundamental beam. These more general phase profiles may be used (1) to improve the nearfield imaging in THI, where the notch in the fundamental field may impact the THI second harmonic field levels, and (2) to improve the behavior in either THI or HCAI when the aperture is truncated by the end of the transducer array.

The embodiments described above are preferably used in combination with classical filtering of the received backscattered signal to select the desired frequency band. The filter requirements are then relaxed and the signal bandwidths may be increased.

This invention can be used with a wide variety of ultrasonic transducers, including 1, 1.5, and 2-dimensional phased arrays, whether flat or curved. The invention can be used with focusing transducers or non-focusing transducers. When mechanically steered, focusing transducers are used, no steering or focusing phases may be required.

Figure 27A:
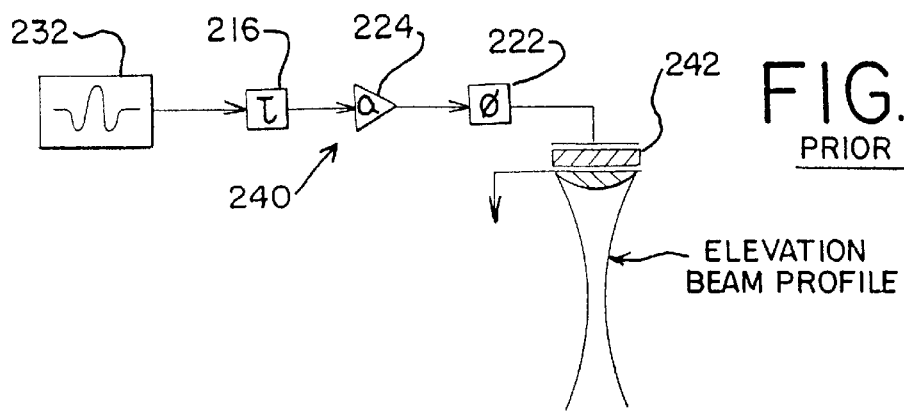
FIGS. 27a and 27b are schematic diagrams of a conventional transmitter signal path (FIG. 27a) and a transmitter signal path characteristic of an embodiment of this invention (FIG. 27b).
Figure 27B:
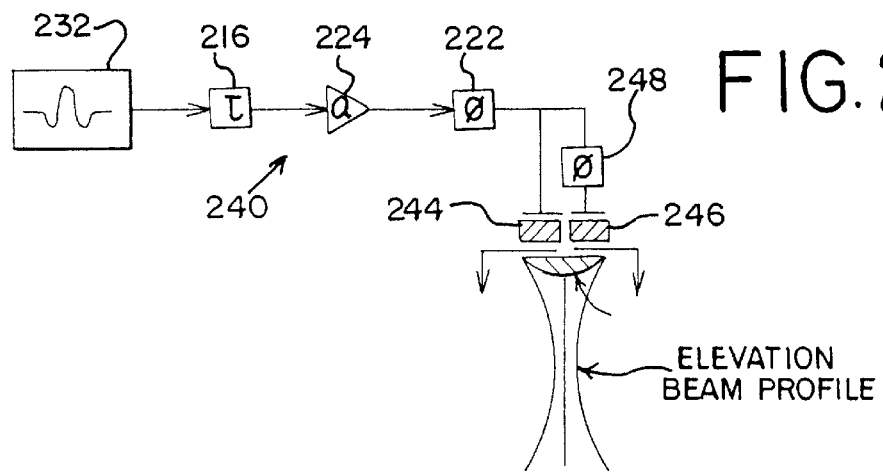

This invention can be implemented in an out-of-plane fashion as opposed to the in-plane fashion described up to this point. That is, instead of splitting the aperture in azimuth (along the length of the transducer array), we split it in elevation (along the width of the transducer array). FIGS. 27a and 27b both show one channel of a multichannel system such as those shown in earlier examples (FIGS. 24–26). What would otherwise be a 1-D transducer array is diced at least once in elevation so that the elevational aperture includes at least two elements 244, 246. FIG. 27a shows a single system transmit channel 240 and transducer element 242 before such dicing, and FIG. 27b shows the modified system and transducer element. A conventional focused and steered signal is sent both directly to one of the elevational sub-elements 244 and also to a phase shifter 248. The signal is shifted in phase by pi for the THI implementation or by pi/2 for the HCAI implementation, and that signal is sent to the second of the elevational sub-elements 246. As before, the resultant null in the transmitted field occurs along the beam axis, but now in elevation as opposed to in azimuth. On receive, the phase shifter 248 is switched out of the signal path and the signals from the two elevational sub-elements 244, 246 are simply summed and sent to the normal receive electronics. As before, the phase difference between the two halves of the aperture is what is important, so another implementation would be to have two phase shifters, one for each elevational subaperture, and use a phase difference of either pi (THI case) or pi/2 (HCAI case). This approach may be used with transducers that are focused in elevation with an acoustic lens or via transducer component curvature. The approach may also be used with transducers that are focused electronically in elevation (i.e., a 2-D array) or that make use of active elevational aperture growth (i.e., a 1.5-D array).

The contrast agent imaging embodiments of this invention may also be used in conjunction with other THI suppression techniques such as transmit waveform predistortion. The pi/2 split-phase aperture approach and the inverse distortion approach may be used together to obtain complementary suppression of the THI signal and to further enhance the contrast between the contrast agent image and the THI image. The HCAI embodiments of the split-phase approach result in a null in the THI signal along the beam axis, but some THI signal will still be present just to either side of the beam axis and will be present in the returned signal. Transmit waveform pre-distortion may be used to reduce the off-axis THI signal and improve the contrast-to-THI signal ratio. It is also expected that some degree of THI signal will be present on-axis due to second harmonic that is generated along the beam axis as the left and right halves of the fundamental field diffract into one-another. This uncancelled THI signal may likewise be reduced via transmit waveform predistortion.

This invention can be implemented using any suitable transmit waveform generator, including analog and digital generators. The fundamental component of the resulting ultrasonic pulses can be positioned as desired in the frequency spectrum, as for example between 1 and 10 MHz. 2.5 MHz is one suitable example of a fundamental component frequency. The selected phase difference does not have to be set precisely at pi or pi/2, but can vary from these values depending on many other considerations, including the steering, focusing and aberration correction phases that are conventionally used in ultrasonic transmit generators.

Figure 28A:
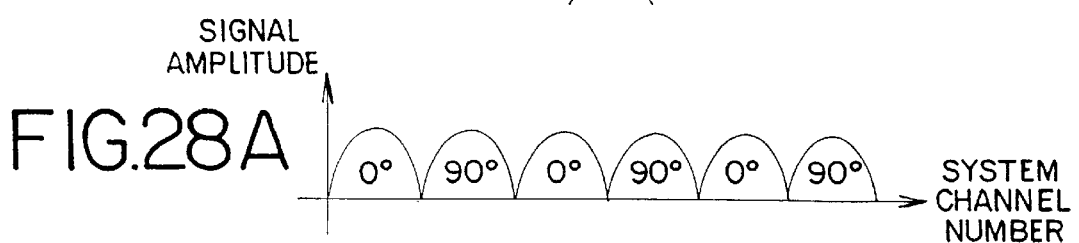
FIGS. 28a, 28b and 28c are apodization diagrams of three embodiments of this invention, showing apodization as a function of position along the azimuthal (X) direction in a phased array transducer.

The preferred embodiments described above use two subapertures that are symmetrically placed across a phased array. Many alternatives are possible. For example, more than two subapertures can be used, and the subapertures may not be individually continuous. For example, transducer elements of a first subaperture may alternate with transducer elements of a second subaperture on a group-of-elements by group-of-elements basis. A simple example of an aperture having six subapertures is shown in FIG. 28a. Each hump represents the apodization of the respective subaperture, and the overall phase associated with each subaperture is noted. Note that the illustrated phasing is that preferred for HCAI embodiments, and that the subaperture apodizations are all identical. If desired, at least some of the subapertures may be asymmetrically positioned on the transducer. Because the desired cancellation is generally spaced from the face of the transducer, each subaperture preferably includes four or more adjacent transducer elements (e.g. transducer elements n, n+1, n+2, . . . n+m, m≧3). This is quite different from the alternate phasing approach disclosed by S. Krishnan et al. in "Transmit Aperture Phasing for Nonlinear Contrast Imaging" (Ultrasonic Imaging 18, 77–105, 1996) which is intended to reduce harmonics generated by the transducer and the transmitter, not the tissue.

Figure 28B:
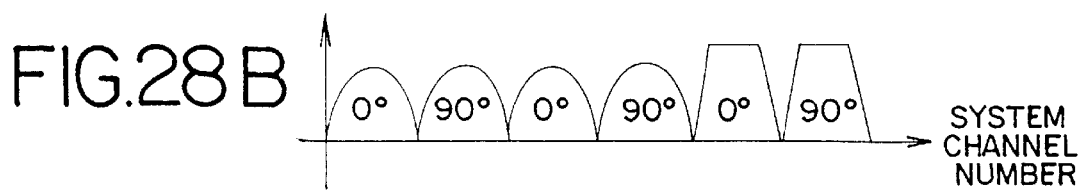
Figure 28C:
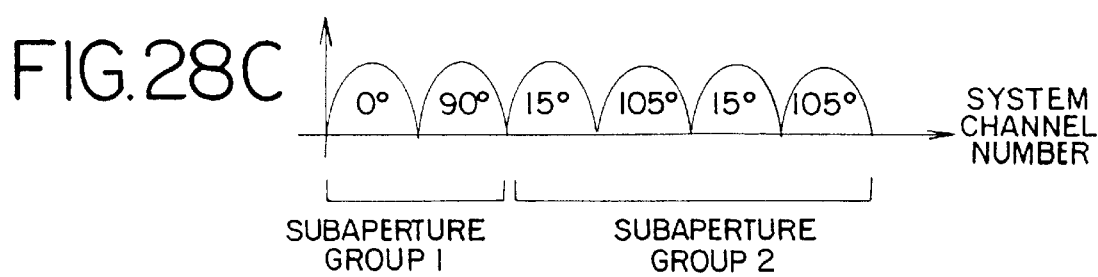

Regardless of the number of subapertures, each subaperture may be apodized and different subapertures may be apodized differently (see FIG. 28b). The sizes of the subapertures may be the same or may differ. In THI embodiments the phases of neighboring subapertures differ by roughly 180 degrees, and in HCAI embodiments they differ by roughly 90 degrees. There may, however, be a first group of two or more subapertures with such a pattern of phasing neighbored by a second group of subapertures, but the pattern of phasing may be broken from one group to the next. An example of such a subaperture scheme is shown in FIG. 28c. Such a subaperture arrangement may be useful for the tuning of the properties of the axial null. The spatial properties of the null, as well as the frequency distribution in the vicinity of the null, may be adjusted by imposing changes in the various parameters introduced above. For example, the adjustment of the apodizations of the subapertures and the shifting the overall phase of one group of subapertures relative to another such group causes changes in the structure of the null.

It should be noted that there exist other phase arrangements that perform the same or similar function as that of the 90 and 180 degree phase difference arrangements discussed above. An example for the case of three subapertures is one in which the left and right subapertures are advanced and retarded in phase, respectively, by 60 degrees with respect to the central aperture. The transmit field on axis (near the transmit focus) is then such that the fundamental fields delivered by these three subapertures add constructively to a substantial, nonzero sum. The second harmonic fields, on the other hand, add destructively to zero. This subaperture arrangement is therefore suited to HCAI. Other subaperture phase arrangements that result in such constructive/destructive response are included in the scope of this invention. For HCAI embodiments, the phasing of the subapertures is such that the fundamental fields generated by the subapertures add constructively on axis (everywhere or just near the transmit focus) and the second harmonic signals generated by the subapertures during propagation add destructively. The constructive addition is sufficiently constructive that the fundamental field has sufficient strength to excite a significant second harmonic response from the contrast agent. For THI embodiments, the phasing of the subapertures is such that the fundamental fields generated by the subapertures add destructively on axis (everywhere or just near the transmit focus) but the resultant second harmonic fields add constructively. In this case, the degree to which the fields add constructively or destructively need only be such that the difference between the second harmonic and fundamental field levels is improved over that of a standard aperture (i.e., the fundamental is suppressed relative to the second harmonic).

There are several advantages of the split-phase aperture approach as compared to the two-pulse approach of the prior art. First, it is a single-firing approach and should therefore have twice the frame rate. Second, the fundamental levels in the transmit field can be reduced, and the transmit power levels may therefore be increased without violation of FDA standards. The result is larger amplitude second harmonic fields, which leads to better signal-to-noise ratios and penetration. Third, the overall received signal levels, which are typically dominated by the fundamental signal, can be reduced without reduction of the second harmonic signal levels. A greater amount of analog gain may therefore be applied upon receive without saturation. This leads to improvements in overall signal dynamic range and therefore SNR. Furthermore, the split-phase aperture approach causes such suppression over an unlimited range.

This invention is well suited for use in tissue harmonic imaging, where no added contrast agent is introduced into the tissue at any time during an entire ultrasonic examination, which will often have a duration of ¼ to ¾ hour.

As used herein, the term "subaperture" is intended to encompass two or more transducer elements arranged in any suitable geometry. Subapertures may be overlapping or non-overlapping in alternative embodiments. For example, partially or completely overlapping subapertures may be especially useful in conjunction with non-hyperbolic delay profiles such as Axicon delay profiles, in which case each subaperture may include all of the transducer elements of the transducer probe.

As used herein in the term "set" is intended broadly to encompass two or more elements.

The foregoing detailed description has discussed only a few of the many alternative forms that this invention can take. It should clearly be understood that many changes and modifications are possible, and that the scope of this invention is not limited to the foregoing specific examples. It is only the following claims, including all equivalents, that are intended to define the scope of this invention.

What is claimed is:

1. In a method comprising the steps of (a) transmitting a plurality of waveforms from a transducer at a fundamental frequency focused at a point and (b) receiving reflected ultrasonic energy at a harmonic of the fundamental frequency, an improvement wherein step (a) comprises the steps of:

(a1) applying said plurality of waveforms to a respective plurality of transducer elements, a first uni-polar waveform of said plurality of waveforms characterized by uniform amplitude and by a first value of a harmonic power ratio, waveforms transmitted from said transducer elements and corresponding to said plurality of waveforms summing as an acoustic waveform substantially at the point, said acoustic waveform characterized by a second value of said harmonic power ratio less than said first value.

2. The method of claim 1 wherein the step (a1) comprises (a2) generating said first waveform as a uniform amplitude signal comprising a first duration and (a3) generating a second waveform of said plurality of waveforms as a uniform amplitude signal comprising a second duration shorter than said first duration, respectively.

3. The method of claim 2 wherein the step (a2) comprises setting a first amplitude of said first waveform different than a second amplitude of said second waveform by a shape amplitude.

4. The method of claim 1 wherein the step (a) further comprises (a2) filtering said plurality of waveforms.

5. The method of claim 1 wherein the step (a1) comprises applying at least a second waveform of said plurality of waveforms to one of said plurality of transducer elements, said second waveform characterized by a third value of said harmonic power ratio greater than said second value of said harmonic power ratio.

6. The method of claim 1 wherein step (a1) comprises delaying said first waveform relative to a second waveform of said plurality of waveforms by a shape delay.

7. The method of claim 6 wherein the step (a1) comprises delaying said first waveform by an integer number of cycles relative to said second waveform, wherein said acoustic waveform comprises a gradually increasing and gradually decreasing shape.

8. The method of claim 6 wherein the step (a1) comprises delaying said first waveform by a fraction of a cycle relative to said second waveform.

9. The method of claim 1 wherein the step (a11) comprises generating said first waveform comprising a first number of cycles and a second waveform of said plurality of waveforms comprising a second number of cycles less than said first number of cycles.

10. The method of claim 9 wherein the step (a1) comprises setting said second number as an integer value at least two less than said first number.

11. The method of claim 10 wherein the step (a11) comprises delaying said second waveform relative to said first waveform by a shape delay comprising a third number of cycles, said third number of cycles substantially half the difference between said first and second numbers, wherein said acoustic waveform comprises a gradually increasing and gradually decreasing shape.

12. The method of claim 1 wherein the step (a1) comprises setting characteristics selected from the group of: (i) a shape delay; (ii) a number of cycles; (iii) a shape amplitude; and (iv) any combination thereof.

13. The method of claim 1 wherein said first waveform and a second waveform of said plurality of waveforms comprise substantially rectangular waveforms characterized by uniform amplitude.

14. The method of claim 1 further comprising the step of providing a contrast agent.

15. The method of claim 1 wherein the step (a1) comprises applying said first waveform to a first group of said transducer elements and transmitting a second waveform of said plurality of waveforms from a second group of said transducer elements.

16. The method of claim 15 wherein the step (a1) comprises applying to said first group comprising a center group of transducer elements.

17. The method of claim 15 wherein the step (a1) comprises applying to said first and second groups comprising alternating transducer elements.

18. The method of claim 1 further comprising the steps of:
(a2) transmitting at least said first waveform, and a second and a third waveform of said plurality of waveforms from at least said first, a second and a third transducer element, respectively, said third waveform characterized by a third value of said harmonic power ratio greater than said second value and relative to at least said first and second waveforms as a function of a shape comprising a sum of said first, second and third waveforms and rising gradually to a respective maximum value and falling gradually from said respective maximum value, said acoustic waveform comprising said shape.

19. The method of claim 1 further comprising the step of (a2) modulating a pulse width of pulses within said first waveform.

20. The method of claim 1 further comprising the step of shaping the amplitude of said first waveform.

21. The method of claim 1 further comprising the step or steps of any combination of two or three of steps a2 and a3:
(a2) modulating a pulse width of at least said first waveform;
(a3) shaping the amplitude of said first waveform.

22. The method of claim 1 wherein step (a) further comprises:
starting transmission for at least three waveforms of the plurality of waveforms as a function of at least three different delays in addition to focusing delays; and
wherein the acoustic waveform is associated with reduced energy at the harmonic of the fundamental frequency, a characteristic of said reduction responsive to the three different delays.

23. The method of claim 1 wherein step (a) further comprises:
transmitting from two groupings of elements the plurality of waveforms, the two groupings selected from groupings consisting of: unequal groupings, groupings comprising at least two adjacent transducer elements and combinations thereof, the waveforms of the plurality of waveforms associated with a first one of the groupings of elements responsive to different delays than the waveforms of the plurality of waveforms associated with a second one of the groupings of elements, a characteristic of said reduction responsive to the grouping of elements.

24. The method of claim 23 wherein step (a) further comprises:
transmitting from the first grouping with delays in addition to focusing delays and from the second grouping with focusing delays.

25. The method of claim 24 wherein step (a) comprises:
transmitting from the first grouping, the first grouping comprising elements non-symmetrical about a center element.

26. An apparatus for transmitting ultrasonic energy at a fundamental frequency focused substantially at a point for receipt of reflected ultrasonic energy at a harmonic of the fundamental frequency comprising:
a transducer comprising a plurality of transducer elements;
a beamformer for applying a plurality of waveforms to said plurality of transducer elements respectively, a first uni-polar waveform of said plurality of waveforms characterized by a uniform amplitude and a first value of a harmonic power ratio, waveforms transmitted from said transducer elements and corresponding to said plurality of waveforms summing as an acoustic waveform substantially at the point, said acoustic waveform characterized by a second value of said harmonic power ratio less than said first value.

27. A method of generating waveforms in the acoustic domain for harmonic imaging comprising the steps of:
transmitting at a first start time at least a first waveform comprising a first number of cycles;
transmitting at a second start time at least a second waveform comprising said first number of cycles, wherein said second start time corresponds to at least a one cycle delay in addition to a focusing delay from said first start time;
said first and second waveforms acoustically summing to contribute to a third waveform at a point, said third waveform comprising a shape rising gradually to a respective value and falling gradually from said respective value.

28. A method of generating waveforms in the acoustic domain for harmonic imaging comprising the steps of:
transmitting at a first start time at least a first waveform comprising a first number of cycles;
transmitting at a second start time at least a second waveform comprising a second number of cycles, wherein said second number of cycles comprises at least two cycles less than said first number and said second start time corresponds to at least a one cycle delay in addition to a focusing delay from said first start time;

said first and second waveforms acoustically summing to contribute to a third waveform at a point, said third waveform comprising a shape rising gradually to a respective value and falling gradually from said respective value.

29. A method of generating waveforms in the acoustic domain for harmonic imaging comprising the steps of:

transmitting at least a first waveform comprising a first amplitude;

transmitting at least a second waveform comprising a second amplitude selected relative to the first amplitude in addition to an apodization amplitude;

said first and second waveforms acoustically summing to contribute to a third waveform at a point, said third waveform comprising a shape rising gradually to a respective value and falling gradually from said respective value and characterized by a number of amplitude levels greater than a number of amplitude levels associated with the first and second waveforms.

30. In a method comprising the steps of (a) transmitting a plurality of waveforms from a transducer at a fundamental frequency focused at a point and (b) receiving reflected ultrasonic energy at a harmonic of the fundamental frequency, an improvement wherein step (a) comprises the steps of:

(a1) starting transmission for at least three waveforms of the plurality of waveforms as a function of at least three different delays in addition to focusing delays;

said at least three waveforms acoustically summing as an acoustic waveform, the acoustic waveform associated with reduced energy at the harmonic of the fundamental frequency, the position of the reduction responsive to the three different delays.

31. The method of claim 30 wherein step (a) further comprises transmitting from two groupings of elements for waveforms associated with respective ones of at least two of the at least three different delays, the two groupings selected from groupings consisting of: unequal groupings, groupings comprising at least two adjacent transducer elements and combinations thereof, a characteristic of said reduction responsive to the grouping of elements.

32. The method of claim 31 wherein step (a) comprises: transmitting the waveforms associated with the three different delays from a first portion of an active aperture and transmitting waveforms associated with focusing delays from a second portion of the active aperture.

33. In a method comprising the steps of (a) transmitting a plurality of waveforms from a transducer at a fundamental frequency focused at a point and (b) receiving reflected ultrasonic energy at a harmonic of the fundamental frequency, an improvement wherein step (a) comprises the steps of:

(a1) transmitting from two groupings of elements waveforms associated with respective ones of at least two different delays, the two groupings selected from groupings consisting of: unequal groupings, grouping comprising at least two adjacent transducer elements and combinations thereof;

said waveforms acoustically summing as an acoustic waveform, the acoustic waveform associated with reduced energy at the harmonic of the fundamental frequency, a characteristic of said reduction responsive to the grouping of elements.

34. The method of claim 33 wherein step (a) further comprises:

starting transmission for at least three waveforms of the plurality of waveforms as a function of at least three different delays in addition to focusing delays;

said at least three waveforms acoustically summing as the acoustic waveform, the position of the reduction responsive to the three different delays.

35. The method of claim 33 wherein step (a) comprises: transmitting from unequal groupings.

36. The method of claim 33 wherein step (a) comprises: transmitting from groupings each comprising at least two adjacent transducer elements.

37. In a method comprising the steps of (a) transmitting a plurality of waveforms from a transducer at a fundamental frequency focused at a point in a target and (b) receiving reflected ultrasonic energy at a harmonic of the fundamental frequency during an imaging session, the target being free of contrast agent during the entire imaging session, an improvement wherein step (a) comprises the steps of:

(a1) applying said plurality of waveforms to a respective plurality of transducer elements during the imaging session, a first waveform of said plurality of waveforms characterized by a first value of a harmonic power ratio, waveforms transmitted from said transducer elements and corresponding to said plurality of waveforms summing as an acoustic waveform substantially at the point, said acoustic waveform characterized by a second value of said harmonic power ratio less than said first value.

38. The method of claim 37 wherein the step (a1) comprises (a2) generating said first waveform as a uniform amplitude signal comprising a first duration and (a3) generating a second waveform of said plurality of waveforms as a uniform amplitude signal comprising a second duration shorter than said first duration, respectively.

39. The method of claim 37 wherein the step (a) further comprises (a2) filtering said plurality of waveforms.

40. The method of claim 37 wherein the step (a1) comprises applying at least a second waveform of said plurality of waveforms to one of said plurality of transducer elements, said second waveform characterized by a third value of said harmonic power ratio greater than said second value of said harmonic power ratio.

41. The method of claim 37 wherein step (a1) comprises delaying said first waveform relative to a second waveform of said plurality of waveforms by a shape delay.

42. The method of claim 41 wherein the step (a1) comprises delaying said first waveform by an integer number of cycles relative to said second waveform, wherein said acoustic waveform comprises a gradually increasing and gradually decreasing shape.

43. The method of claim 41 wherein the step (a1) comprises delaying said first waveform by a fraction of a cycle relative to said second waveform.

44. The method of claim 37 wherein the step (a11) comprises generating said first waveform comprising a first number of cycles and a second waveform of said plurality of waveforms comprising a second number of cycles less than said first number of cycles.

45. The method of claim 44 wherein the step (a1) comprises setting said second number as an integer value at least two less than said first number.

46. The method of claim 45 wherein the step (a1) comprises delaying said second waveform relative to said first waveform by a shape delay comprising a third number of cycles, said third number of cycles substantially half the difference between said first and second numbers, wherein said acoustic waveform comprises a gradually increasing and gradually decreasing shape.

47. The method of claim 37 wherein the step (a2) comprises setting a first amplitude of said first waveform different than a second amplitude of said second waveform by a shape amplitude.

48. The method of claim 37 wherein the step (a1) comprises setting characteristics selected from the group of: (i) a shape delay; (ii) a number of cycles; (iii) a shape amplitude; and (iv) any combination thereof.

49. The method of claim 37 wherein at least said first waveform and a second waveform of said plurality of waveforms comprise uni-polar waveforms characterized by uniform amplitude.

50. The method of claim 37 wherein at least said first waveform and a second waveform of said plurality of waveforms comprise bi-polar waveforms characterized by uniform amplitude.

51. The method of claim 37 wherein said first waveform and a second waveform of said plurality of waveforms comprise substantially rectangular waveforms characterized by uniform amplitude.

52. The method of claim 37 wherein said first waveform and a second waveform of said plurality of waveforms comprise sinusoidal waveforms characterized by uniform amplitude.

53. The method of claim 37 wherein the step (a1) comprises applying said first waveform to a first group of said transducer elements and transmitting a second waveform of said plurality of waveforms from a second group of said transducer elements.

54. The method of claim 53 wherein the step (a1) comprises applying to said first group comprising a center group of transducer elements.

55. The method of claim 53 wherein the step (a1) comprises applying to said first and second groups comprising alternating transducer elements.

56. The method of claim 37 further comprising the steps of:
   (a2) transmitting at least said first waveform, and a second and a third waveform of said plurality of waveforms from at least said first, a second and a third transducer element, respectively, said third waveform characterized by a third value of said harmonic power ratio greater than said second value and relative to at least said first and second waveforms as a function of a shape comprising a sum of said first, second and third waveforms and rising gradually to a respective maximum value and falling gradually from said respective maximum value, said acoustic waveform comprising said shape.

57. The method of claim 37 further comprising the step of (a1) modulating a pulse width of pulses within said first waveform.

58. The method of claim 37 further comprising the step of shaping the amplitude of said first waveform.

59. The method of claim 37 further comprising the step or steps of any combination of two or three of steps a2 and a3:
   (a2) modulating a pulse width of at least said first waveform;
   (a3) shaping the amplitude of said first waveform.

60. The method of claim 37 wherein step (a) further comprises:
   starting transmission for at least three waveforms of the plurality of waveforms as a function of at least three different delays in addition to focusing delays;
   the acoustic waveform associated with reduced energy at the harmonic of the fundamental frequency, a characteristic of said reduction responsive the three different delays.

61. The method of claim 37 wherein step (a) further comprises:
   transmitting from two groupings of elements the plurality of waveforms, the two groupings selected from groupings consisting of: unequal groupings, groupings comprising at least two adjacent transducer elements and combinations thereof, the waveforms of the plurality of waveforms associated with one of the groupings of elements responsive to different delays than the waveforms of the plurality of waveforms associated with a second one of the groupings of elements, a characteristic of said reduction responsive to the grouping of elements.

62. The method of claim 61 wherein step (a) further comprises:
   transmitting from the first grouping with delays in addition to focusing delays and from the second grouping with focusing delays.

63. The method of claim 62 wherein step (a) comprises:
   transmitting from the first grouping, the first grouping comprising elements non-symmetrical about a center element.

64. In a method comprising the steps of (a) transmitting a plurality of waveforms from a transducer at a fundamental frequency into a target for each of a plurality of scan lines and (b) receiving reflected ultrasonic energy at a harmonic of the fundamental frequency response to step (a), an improvement wherein step (a) comprises the steps of:
   (a1) changing an aperture for transmitting waveforms with different delays in addition to focusing delays as a function of an angle of one of said plurality of scan lines.

65. The method of claim 64 wherein step (a1) comprises changing the aperture to at least three different sizes for at least three respective groups of said plurality of scan lines, the three groups comprising a center group, an intermediate group and an edge group.

66. The method of claim 64 wherein step (a1) comprises changing the aperture from a full aperture to no aperture.

67. The method of claim 66 wherein step (a1) comprises decreasing the aperture as a function of the angle away from a center scan line of said plurality of scan lines.

68. The method of claim 64 wherein step (a) comprises:
   (a2) changing another aperture for transmitting waveforms with focusing delays as a function of the aperture of step (a1).

69. The method of claim 68 wherein step (a) comprises:
   placing the aperture of step (a1) off-set from a center of an active aperture.

70. In a method comprising the steps of (a) transmitting a plurality of waveforms from a transducer at a fundamental frequency into a target for each of a plurality of scan lines and (b) receiving reflected ultrasonic energy at a harmonic of the fundamental frequency response to step (a), an improvement wherein step (a) comprises the steps of:
   (a1) changing an aperture for transmitting waveforms with different phases in addition to focusing delays as a function of an angle of one of said plurality of scan lines.

71. The method of claim 70 wherein step (a11) comprises changing the aperture to at least three different sizes for at least three respective groups of said plurality of scan lines, the three groups comprising a center group, an intermediate group and an edge group.

72. The method of claim 70 wherein step (a1) comprises changing the aperture from a full aperture to no aperture.

73. The method of claim 72 wherein step (a1) comprises decreasing the aperture as a function of the angle away from a center scan line of said plurality of scan lines.

* * * * *

UNITED STATES PATENT AND TRADEMARK OFFICE
CERTIFICATE OF CORRECTION

PATENT NO. : 6,193,659 B1
DATED : February 27, 2001
INVENTOR(S) : B. S. Ramamurthy et al.

It is certified that error appears in the above-identified patent and that said Letters Patent is hereby corrected as shown below:

<u>Title page,</u>
Item [75], Inventors, delete "Charles Bradley, Burlingame;".

<u>Column 23,</u>
Lines 1 and 9, delete "(all)" and substitute -- (a1) -- in its place.

<u>Column 26,</u>
Line 54, delete "(all)" and substitute -- (a1) -- in its place.

<u>Column 28,</u>
Line 57, delete "(all)" and substitute -- (a1) -- in its place.

Signed and Sealed this

Tenth Day of December, 2002

JAMES E. ROGAN
*Director of the United States Patent and Trademark Office*